(12) United States Patent
Lucisano et al.

(10) Patent No.: US 10,638,962 B2
(45) Date of Patent: May 5, 2020

(54) BIO-ADAPTABLE IMPLANTABLE SENSOR APPARATUS AND METHODS

(71) Applicant: GlySens Incorporated, San Diego, CA (US)

(72) Inventors: Joseph Lucisano, San Diego, CA (US); Timothy Routh, San Diego, CA (US); Joe Lin, San Diego, CA (US)

(73) Assignee: GlySens Incorporated, San Diego, CA (US)

(*) Notice: Subject to any disclaimer, the term of this patent is extended or adjusted under 35 U.S.C. 154(b) by 363 days.

(21) Appl. No.: 15/197,104

(22) Filed: Jun. 29, 2016

(65) Prior Publication Data

US 2018/0000395 A1   Jan. 4, 2018

(51) Int. Cl.
*A61B 5/1486* (2006.01)
*A61B 5/145* (2006.01)
*A61B 5/00* (2006.01)

(52) U.S. Cl.
CPC ...... *A61B 5/14865* (2013.01); *A61B 5/14532* (2013.01); *A61B 5/6861* (2013.01);
(Continued)

(58) Field of Classification Search
CPC ............ A61B 5/14865; A61B 5/14532; A61B 5/6861; A61B 2562/162; A61B 2562/18; A61B 2562/247
(Continued)

(56) References Cited

U.S. PATENT DOCUMENTS 2,508,523 A   5/1950 Krebs
2,563,062 A   8/1951 Perley
(Continued)

FOREIGN PATENT DOCUMENTS

CN   1355670 A   6/2002
CN   1592570 A   3/2005
(Continued)

OTHER PUBLICATIONS

Dhakar L., "Skin Based Flexible Triboelectric Nanogenerators with Motion Sensing Capability," Micro Electro Mechanical Systems (MEMS), 2015 28th IEEE International Conference on, 2015, IEEE, pp. 106-109.
(Continued)

*Primary Examiner* — Navin Natnithithadha
(74) *Attorney, Agent, or Firm* — Gazdzinski & Associates, PC

(57) ABSTRACT

Biocompatible implantable sensor apparatus and methods of implantation and use. In one embodiment, the sensor apparatus is an oxygen-based glucose sensor having biocompatibility features that mitigate the host tissue response. In one variant, these features include use of a non-enzymatic membrane over each of the individual analyte detectors so as to preclude contact of the surrounding tissue with the underlying enzyme or other matrix, and mitigate vascularization, and insulation of the various electrodes and associated electrolytic processes of the sensor from the surrounding tissue. In one implementation, the sensor region of the implanted apparatus is configured to interlock or imprint the surrounding tissue so as to promote a high degree of glucose molecule diffusion into the individual detectors, and a constant and predictable sensor to blood vessel interface, yet preclude the tissue from bonding to the sensor, especially over extended periods of implant.

43 Claims, 7 Drawing Sheets

(52) U.S. Cl.
CPC ..... *A61B 2562/162* (2013.01); *A61B 2562/18* (2013.01); *A61B 2562/247* (2013.01)

(58) Field of Classification Search
USPC ........................................ 600/309, 345–365
See application file for complete search history.

(56) References Cited

U.S. PATENT DOCUMENTS

| | | | |
|---|---|---|---|
| 2,805,191 A | 9/1957 | Hersch | |
| 2,864,750 A | 12/1958 | Hughes, Jr. et al. | |
| 2,998,371 A | 8/1961 | Sabins | |
| 3,099,575 A | 7/1963 | Hill | |
| 3,246,235 A | 4/1966 | Allsopp | |
| 3,249,250 A | 5/1966 | McKee | |
| 3,300,345 A | 1/1967 | Lyons, Jr. | |
| 3,308,046 A | 3/1967 | Suleski | |
| 3,458,421 A | 7/1969 | Harald | |
| 3,505,195 A | 4/1970 | Borge et al. | |
| 3,542,662 A | 11/1970 | Hicks et al. | |
| 3,616,412 A | 10/1971 | Oliver | |
| 3,957,613 A | 5/1976 | Macur | |
| 4,036,716 A | 7/1977 | Hulthe | |
| 4,088,550 A | 5/1978 | Malkin | |
| 4,240,438 A | 12/1980 | Shults et al. | |
| 4,306,952 A | 12/1981 | Jansen | |
| 4,340,457 A | 7/1982 | Kater | |
| 4,361,153 A | 11/1982 | Slocum et al. | |
| 4,366,033 A | 12/1982 | Richter et al. | |
| 4,431,004 A | 2/1984 | Bessman et al. | |
| 4,458,686 A | 7/1984 | Clark, Jr. | |
| 4,484,987 A | 11/1984 | Gough | |
| 4,494,950 A | 1/1985 | Fischell | |
| 4,541,431 A | 9/1985 | Ibrahim et al. | |
| 4,550,732 A | 11/1985 | Batty, Jr. et al. | |
| 4,553,547 A | 11/1985 | Keimel | |
| 4,571,589 A | 2/1986 | Slocum et al. | |
| 4,637,861 A | 1/1987 | Krull et al. | |
| 4,650,547 A | 3/1987 | Gough | |
| 4,671,288 A | 6/1987 | Gough | |
| 4,703,756 A | 11/1987 | Gough et al. | |
| 4,746,218 A | 5/1988 | Lord, III | |
| 4,748,562 A | 5/1988 | Miller et al. | |
| 4,759,828 A | 7/1988 | Young et al. | |
| 4,781,798 A | 11/1988 | Gough | |
| 4,830,713 A | 5/1989 | Gagescu | |
| 4,890,620 A | 1/1990 | Gough | |
| 5,042,902 A | 8/1991 | Huebscher et al. | |
| 5,046,242 A | 9/1991 | Kuzma | |
| 5,077,476 A | 12/1991 | Rosenthal | |
| 5,105,811 A | 4/1992 | Kuzma | |
| 5,112,455 A | 5/1992 | Cozzette et al. | |
| 5,150,516 A | 9/1992 | Boero et al. | |
| 5,165,406 A | 11/1992 | Wong | |
| 5,189,717 A | 2/1993 | Larson et al. | |
| 5,264,103 A | 11/1993 | Matsushita | |
| 5,272,283 A | 12/1993 | Kuzma | |
| 5,273,203 A | 12/1993 | Webster | |
| 5,283,104 A | 2/1994 | Aoude et al. | |
| 5,283,204 A | 2/1994 | Rhodes et al. | |
| 5,284,140 A | 2/1994 | Allen et al. | |
| 5,322,063 A | 6/1994 | Allen et al. | |
| 5,337,475 A | 8/1994 | Aoude et al. | |
| 5,395,504 A | 3/1995 | Asulab | |
| 5,431,160 A | 7/1995 | Wilkins | |
| 5,487,855 A | 1/1996 | Moeggenborg et al. | |
| 5,497,772 A | 3/1996 | Schulman et al. | |
| 5,560,098 A | 10/1996 | Robins | |
| 5,660,163 A | 8/1997 | Schulman et al. | |
| 5,692,299 A | 12/1997 | Daems et al. | |
| 5,695,623 A | 12/1997 | Michel et al. | |
| 5,711,861 A | 1/1998 | Ward et al. | |
| 5,727,283 A | 3/1998 | Webster | |
| 5,741,330 A * | 4/1998 | Brauker ................ | A61F 2/022 424/422 |
| 5,750,926 A | 5/1998 | Schulman et al. | |
| 5,776,324 A | 7/1998 | Usala | |
| 5,777,060 A | 7/1998 | Van Antwerp | |
| 5,782,755 A | 7/1998 | Chance et al. | |
| 5,782,891 A | 7/1998 | Hassler et al. | |
| 5,791,344 A | 8/1998 | Mann | |
| 5,804,048 A | 9/1998 | Wong et al. | |
| 5,821,011 A | 10/1998 | Taylor et al. | |
| 5,842,983 A | 12/1998 | Fresenius | |
| 5,855,995 A | 1/1999 | Haq et al. | |
| 5,864,088 A | 1/1999 | Sato et al. | |
| 5,882,494 A | 3/1999 | Van Antwerp | |
| 5,887,240 A | 3/1999 | Fournier et al. | |
| 5,932,175 A | 8/1999 | Knute et al. | |
| 5,942,842 A | 8/1999 | Fogle, Jr. | |
| 5,964,993 A | 10/1999 | Blubaugh, Jr. et al. | |
| 5,985,129 A | 11/1999 | Gough et al. | |
| 6,001,067 A | 12/1999 | Shults | |
| 6,027,479 A | 2/2000 | Alei et al. | |
| 6,041,496 A | 3/2000 | Haq et al. | |
| 6,081,736 A | 6/2000 | Colvin et al. | |
| 6,090,503 A | 7/2000 | Taylor et al. | |
| 6,096,066 A | 8/2000 | Chen et al. | |
| 6,107,083 A | 8/2000 | Collins et al. | |
| 6,119,208 A | 9/2000 | White et al. | |
| 6,193,421 B1 | 2/2001 | Tamekuni et al. | |
| 6,200,772 B1 | 3/2001 | Vadgama et al. | |
| 6,212,416 B1 | 4/2001 | Ward et al. | |
| 6,221,513 B1 | 4/2001 | Lasater | |
| 6,403,944 B1 | 6/2002 | MacKenzie et al. | |
| 6,466,810 B1 | 10/2002 | Ward et al. | |
| 6,516,808 B2 | 2/2003 | Schulman | |
| 6,551,252 B2 | 4/2003 | Sackner et al. | |
| 6,558,321 B1 | 5/2003 | Burd et al. | |
| 6,642,015 B2 | 11/2003 | Vachon et al. | |
| 6,721,587 B2 | 4/2004 | Gough | |
| 6,741,877 B1 | 5/2004 | Shults et al. | |
| 6,809,607 B2 | 10/2004 | Nagasaka | |
| 6,812,404 B1 | 11/2004 | Martinez | |
| 6,832,114 B1 | 12/2004 | Whitehurst et al. | |
| 6,843,107 B2 | 1/2005 | Newman et al. | |
| 6,931,268 B1 | 8/2005 | Kiani-Azarbayjany et al. | |
| 7,005,796 B2 | 2/2006 | Kolluri et al. | |
| 7,079,881 B2 | 7/2006 | Schulman et al. | |
| 7,106,939 B2 | 9/2006 | Labrake et al. | |
| 7,110,803 B2 | 9/2006 | Shults et al. | |
| 7,134,999 B2 | 11/2006 | Brauker et al. | |
| 7,136,689 B2 | 11/2006 | Shults et al. | |
| 7,140,787 B2 | 11/2006 | Yamauchi et al. | |
| 7,146,203 B2 | 12/2006 | Botvinick et al. | |
| 7,161,727 B2 | 1/2007 | Callies et al. | |
| 7,189,341 B2 | 3/2007 | Li et al. | |
| 7,192,450 B2 | 3/2007 | Brauker et al. | |
| 7,226,978 B2 | 6/2007 | Tapsak et al. | |
| 7,248,912 B2 | 7/2007 | Gough et al. | |
| 7,323,142 B2 | 1/2008 | Pendo et al. | |
| 7,336,984 B2 | 2/2008 | Gough et al. | |
| 7,460,898 B2 | 12/2008 | Brister et al. | |
| 7,467,003 B2 | 12/2008 | Brister et al. | |
| 7,471,972 B2 | 12/2008 | Rhodes et al. | |
| 7,480,988 B2 | 1/2009 | Ok et al. | |
| 7,497,827 B2 * | 3/2009 | Brister ................ | A61B 5/0002 600/309 |
| 7,514,791 B2 | 4/2009 | Shah et al. | |
| 7,525,298 B2 | 4/2009 | Morgan et al. | |
| 7,761,130 B2 | 7/2010 | Simpson et al. | |
| 7,857,760 B2 * | 12/2010 | Brister ................ | A61B 5/0031 600/365 |
| 7,871,456 B2 | 1/2011 | Gough et al. | |
| 7,875,293 B2 * | 1/2011 | Shults ................ | A61B 5/14532 424/424 |
| 7,881,763 B2 | 2/2011 | Brauker et al. | |
| 7,894,870 B1 | 2/2011 | Lucisano et al. | |
| 8,133,178 B2 * | 3/2012 | Brauker ................ | A61B 5/1411 600/365 |
| 8,270,661 B2 ‡ | 9/2012 | Sorensen | |
| 8,357,107 B2 | 1/2013 | Draudt et al. | |
| 8,690,820 B2 | 4/2014 | Cinar et al. | |
| 8,763,245 B1 | 7/2014 | Lucisano et al. | |
| 9,002,711 B2 ‡ | 4/2015 | Morinaka et al. | |

(56) References Cited

U.S. PATENT DOCUMENTS

| | | |
|---|---|---|
| 9,119,528 B2 ‡ | 9/2015 | Cobelli et al. |
| 9,247,901 B2 | 2/2016 | Kamath et al. |
| 9,325,060 B2 | 4/2016 | Kalistaja et al. |
| 9,362,776 B2 ‡ | 6/2016 | Low et al. |
| 9,444,027 B2 ‡ | 9/2016 | Dibra et al. |
| 9,451,908 B2 | 9/2016 | Kamath et al. |
| 2002/0026108 A1 | 2/2002 | Colvin et al. |
| 2002/0123087 A1 | 9/2002 | Vachon et al. |
| 2002/0156355 A1 | 10/2002 | Gough |
| 2002/0161286 A1 | 10/2002 | Gerber et al. |
| 2002/0193671 A1 | 12/2002 | Ciurczak et al. |
| 2003/0048621 A1 | 3/2003 | Blood et al. |
| 2003/0049166 A1 | 3/2003 | Pendo et al. |
| 2003/0053784 A1 | 3/2003 | Labrake et al. |
| 2003/0126593 A1 | 7/2003 | Mault |
| 2003/0179167 A1 | 9/2003 | Kolluri et al. |
| 2003/0181794 A1 | 9/2003 | Rini et al. |
| 2003/0187338 A1 | 10/2003 | Say et al. |
| 2003/0217966 A1 | 11/2003 | Tapsak et al. |
| 2003/0228681 A1 | 12/2003 | Ritts et al. |
| 2004/0011671 A1* | 1/2004 | Shults ............... A61B 5/0031 205/777.5 |
| 2004/0012935 A1 | 1/2004 | Tagi et al. |
| 2004/0057043 A1 | 3/2004 | Newman et al. |
| 2004/0064133 A1 | 4/2004 | Miller et al. |
| 2004/0106857 A1 | 6/2004 | Gough et al. |
| 2004/0158194 A1 | 8/2004 | Wolff et al. |
| 2004/0167080 A1 | 8/2004 | Dodge et al. |
| 2004/0176669 A1 | 9/2004 | Colvin et al. |
| 2004/0190111 A1 | 9/2004 | Callies et al. |
| 2004/0199059 A1 | 10/2004 | Brauker et al. |
| 2004/0220459 A1 | 11/2004 | Schlegel et al. |
| 2005/0027175 A1 | 2/2005 | Yang |
| 2005/0031689 A1* | 2/2005 | Shults ............... A61B 5/14532 424/473 |
| 2005/0033132 A1* | 2/2005 | Shults ............... A61B 5/14532 600/347 |
| 2005/0052858 A1 | 3/2005 | Shima et al. |
| 2005/0059871 A1 | 3/2005 | Gough et al. |
| 2005/0124873 A1* | 6/2005 | Shults ............... A61B 5/0031 600/345 |
| 2005/0154271 A1 | 7/2005 | Rasdal et al. |
| 2005/0177036 A1* | 8/2005 | Shults ............... A61B 5/14532 600/347 |
| 2005/0196322 A1 | 9/2005 | Truex et al. |
| 2005/0245799 A1 | 11/2005 | Brauker et al. |
| 2005/0245971 A1 | 11/2005 | Brockway et al. |
| 2005/0251083 A1* | 11/2005 | Carr-Brendel ......... A61L 31/10 602/41 |
| 2005/0272989 A1 | 12/2005 | Shah et al. |
| 2006/0085137 A1 | 4/2006 | Bartkowiak et al. |
| 2006/0086624 A1 | 4/2006 | Tapsak et al. |
| 2006/0195029 A1 | 8/2006 | Shults et al. |
| 2006/0204536 A1 | 9/2006 | Shults et al. |
| 2006/0257995 A1* | 11/2006 | Simpson ............ A61B 5/14532 435/287.2 |
| 2006/0257996 A1* | 11/2006 | Simpson ............ A61B 5/14532 435/287.2 |
| 2006/0263763 A1* | 11/2006 | Simpson ............ A61B 5/14532 435/4 |
| 2007/0151868 A1 | 7/2007 | Staib et al. |
| 2008/0033269 A1 | 2/2008 | Zhang |
| 2008/0033272 A1 ‡ | 2/2008 | Gough et al. |
| 2008/0039702 A1 | 2/2008 | Hayter et al. |
| 2008/0197024 A1* | 8/2008 | Simpson ............ A61B 5/14542 205/778 |
| 2008/0200791 A1* | 8/2008 | Simpson ............ A61B 5/14542 600/365 |
| 2008/0317276 A1 ‡ | 12/2008 | Sorensen et al. |
| 2009/0281399 A1 | 11/2009 | Keel et al. |
| 2010/0041971 A1 | 2/2010 | Goode, Jr. et al. |
| 2010/0145317 A1 | 6/2010 | Laster et al. |
| 2010/0149042 A1 | 6/2010 | Utsi et al. |
| 2011/0137142 A1 | 6/2011 | Lucisano et al. |
| 2012/0262298 A1 | 10/2012 | Bohm et al. |
| 2012/0283960 A1 | 11/2012 | Budiman |
| 2012/0323100 A1 | 12/2012 | Kamath et al. |
| 2013/0016573 A1 | 1/2013 | Goel et al. |
| 2013/0030273 A1 | 1/2013 | Tapsak et al. |
| 2013/0172692 A1 | 7/2013 | Choi et al. |
| 2013/0178727 A1 | 7/2013 | Hayter et al. |
| 2013/0197332 A1* | 8/2013 | Lucisano ............ A61B 5/0031 600/345 |
| 2014/0046148 A1 | 2/2014 | Simpson et al. |
| 2014/0309510 A1 | 10/2014 | Lucisano et al. |
| 2014/0323960 A1 | 10/2014 | Sloan |
| 2014/0350652 A1 | 11/2014 | Suwito |
| 2015/0163602 A1 | 6/2015 | Pedersen et al. |
| 2015/0250429 A1 ‡ | 9/2015 | Hampapuram et al. |
| 2015/0289823 A1 ‡ | 10/2015 | Rack-Gomer et al. |
| 2015/0335285 A1 | 11/2015 | Poon et al. |
| 2016/0022180 A1 | 1/2016 | Joseph et al. |
| 2016/0073964 A1 | 3/2016 | Cobelli et al. |
| 2016/0134980 A1 ‡ | 5/2016 | Abolfathi |
| 2016/0163174 A1 | 6/2016 | Zhang et al. |
| 2016/0235300 A1 | 8/2016 | Goodnow |
| 2016/0317744 A1 | 11/2016 | Rule |
| 2017/0173262 A1 | 6/2017 | Veltz |
| 2017/0181628 A1 | 6/2017 | Burnette et al. |
| 2017/0181630 A1 | 6/2017 | Mahalingam et al. |
| 2017/0181674 A1 | 6/2017 | Lucisano et al. |
| 2017/0325725 A1 | 11/2017 | Shah et al. |
| 2017/0347932 A1* | 12/2017 | Lucisano ............ A61B 5/0031 |
| 2017/0357776 A1 | 12/2017 | Baker et al. |
| 2018/0140239 A1* | 5/2018 | Lucisano ........... A61B 5/14865 |
| 2018/0153450 A1* | 6/2018 | Routh ................ A61B 5/076 |

FOREIGN PATENT DOCUMENTS

| | | |
|---|---|---|
| CN | 101006374 A | 7/2007 |
| CN | 201207090 Y | 3/2009 |
| EP | 0852414 B1 | 11/2004 |
| JP | H11295556 A | 10/1999 |
| JP | 2000121863 A | 4/2000 |
| JP | 2005308982 A | 11/2005 |
| JP | 2007121886 A | 5/2007 |
| WO | WO-9213271 A1 | 8/1992 |
| WO | WO-2008013881 A2 | 1/2008 |
| WO | WO-2010-002502 A2 | 1/2010 |
| WO | WO-2011018407 A1 | 2/2011 |
| WO | WO-2011120014 A1 | 9/2011 |
| WO | WO-2013016573 A1 ‡ | 1/2013 |
| WO | WO-2014035672 A2 | 3/2014 |

OTHER PUBLICATIONS

Lemey S., et al., "Wearable Flexible Lightweight Modular RFID Tag With Integrated Energy Harvester," IEEE Transactions on Microwave Theory and Techniques, 2016, vol. 64.7, pp. 2304-2314.

Takei K., et al., "Design for a 400-MHz Passive RFID Prototype System for Long Range Applications," to be published in Proc. IEEE Int. Symp. Antennas Propag. 2007.

Alvarez-Icaza M., et al., "Mass Production of Biosensors," Analytical Chemistry, 1993, vol. 65 (11), pp. 525-533.

Anderson J.M., "Biological Responses to Materials." Annual Review of Materials Research, 2001, vol. 31, pp. 81-110.

Armour J.C., et al., "Application of a Chronic intravascular Blood Glucose Sensor in Dogs," Diabetes, 1990, vol. 39 (12), pp. 1519-1526.

Bard A.J., et al., "Electrochemical Methods: Fundamentals and Applications," 2nd Edition, 2000.

Bilitewski U., et al., "Glucose Biosensors Based on Thick Film Technology," Biosensors and Bioelectronics, 1991, vol. 6, pp. 369-373.

Bremer T.M., et al., "Benchmark Data from the Literature for Evaluation of New Glucose Sensing Technologies," Diabetes Technology and therapeutics, 2001, vol. 3 (3), pp. 409-418.

Cha, C.S., et al., "Electrochemical Behaviour of Microfabricated Thick-film Electrodes," Sensors and Actuators B., 1990, vol. 2, pp. 277-281.

(56) References Cited

OTHER PUBLICATIONS

Choleau, et al., "Calibration of a Subcutaneous Amperometric Glucose Sensor Implanted for 7 Days in Diabetic Patients Part 2. Superiority of the One-point Calibration Method," Biosensors and Bioelectronics, 2002, vol. 17, pp. 641-646.
Choleau, et al., "Calibration of a Subcutaneous Amperometric Glucose Sensor Part 1. Effect of Measurement Uncertainties on the Determination of Sensor Sensitivity and Background Current.," Biosensors and Bioelectronics, 2002, vol. 17, pp. 647-654.
Conway M.J., et al., "Radio Telemetry of Blood Po2 in Vivo," Biomedical Engineering, 1973, vol. 8 (10), pp. 428-430.
Co-pending U.S. Appl. No. 14/982,346, filed Dec. 29, 2015.
Co-pending U.S. Appl. No. 15/170,571, filed Jun. 1, 2016.
Co-pending U.S. Appl. No. 60/269,169, filed Feb. 15, 2001.
Co-pending U.S. Appl. No. 60/423,220, filed Oct. 31, 2002.
Co-pending U.S. Appl. No. 61/511,930, filed Jul. 26, 2011.
Data Sheet—Platinum Oxygen Sensor Materials, Component Metallizations, OS1/OS2/OS3, Heraeus.
Data Sheet Cermet Platinum Conductor data sheet, 5542 Print GD, 5542 Pouring GD, Electro-Science Laboratories,lnc.
Data Sheet-4082 and 3804 Platinum Conductors, MEMS Sensor Materials, Ferro Electronic Materials.
Dutronc, P., et al., "Influence of the Nature of the Screen-printed Electrode Metal on the Transport and Detection Properties of Thick-film Semiconductor Gas Sensors," Sensors and Actuators B, 1992, vol. 6, pp. 279-284.
Fischer U., et al., "A Membrane Combination for Implantable Glucose Sensors. Measurements in Undiluted Biological Fluids," Transactions—American Society for Artificial Internal Organs, 1982, vol. 28, pp. 245-248.
Golonka L.J., et al., "The influence of the Electrode Material on the Sensitivity of an $Sno_2$ Thick-film Gas Sensor," Sensors and Actuators B, 1994, vol. 18-19, pp. 453-456.
Gough D.A., et al., "A Novel Rotated Disc Electrode and Time Lag Method for Characterizing Mass Transport in Liquid-membrane Systems," Journal of the American Institute of Chemical Engineers, 1980, vol. 26, pp. 1013.
Gough D.A., et al., "Membrane-covered, Rotated Disc Electrode," Analytical Chemistry, 1979, vol. 51, pp. 439-444.
Gough D.A., et al., "Two-Dimensional Enzyme Electrode Sensor for Glucose," Analytical Chemistry, 1985, vol. 57 (12), pp. 2351-2357.
Holc J., et al., "Interaction Between Thick-film Platinum Electrodes and Yttria-stabilized $Zro_2$ Ceramic," Journal of Materials Science Letters, 1989, vol. 8, pp. 635-637.
Jablecki M., et al., "Simulations of the Frequency Response of Implantable Glucose Sensors," Analytical Chemistry, 2000, vol. 72 (8), pp. 1853-1859.
Kovatchev B.P., et al., "Graphical and Numerical Evaluation of Continuous Glucose Sensing Time Lag," Diabetes Technology Therapeutics, 2009, vol. 11(3), pp. 139-143.
Leypoldt J.K., et al., "Diffusion and the Limiting Substrate in Two-substrate Immobilized Enzyme Systems," Biotechnology and Bioengineering, 1982, vol. 24 (12), pp. 2705-2719.

Leypoldt J.K., et al., "Model of a Two-substrate Enzyme Electrode for Glucose," Analytical Chemistry, 1984, vol. 56 (14), pp. 2896-2904.
Lucisano, et al., "In Vitro Stability of an Oxygen Sensor," Analytical Chemistry, 1987, vol. 59 (5), pp. 736-739.
Ma, et al., "A Biocompatible and Biodegradable Protein Hydrogel with Green and Red Autofluorescence: Preparation, Characterization and In Vivo Biodegradation Tracking and Modeling," Scientific Reports (Nature.com) published Jan. 27, 2016.
Makale M.T., et al., "Tissue Window Chamber System for Validation of Implanted Oxygen Sensors," American Journal of Physiology. Heart and Circulatory Physiology, 2003, vol. 284 (6), pp. 2288-2294.
McKean B.D., et al., "A Telemetry-Instrumentation System for Chronically Implanted Glucose and Oxygen Sensors," IEEE Transactions on Biomedical Engineering, 1988, vol. 35 (7), pp. 526-532.
Rich A., "Shielding and Guarding," Analog Dialogue, 1983, vol. 17 (1), pp. 8-13.
Sargent B.J., et al., "Design and Validation of the Transparent Oxygen Sensor Array," Biomedical Engineering, IEEE Transactions on, 1991, vol. 38 (5), pp. 476-482.
Elisa Kit Manual Human C3a #550499.
Elisa Kit Manual Human C4a #5550947.
Gough, et al., "Function of an Implanted Tissue Glucose Sensor for More than 1 Year in Animals", Science Translational Medicine, Jul. 28, 2010, vol. 2 (42), pp. 42ra53.
Holmes, et al., Handbook of Thick Film Technology, Electrochemical Publications Ltd (Glasgow: Bell and Bain Ltd., 1976).
Kroschwitz J., "Concise encyclopedia of polymer science and engineering," John Wiley, 1990, pp. 599-1341.
Lucisano, Ph.D. Dissertation, Univ. Of Calif. (San Diego), pp. xv-xvi, 8-10, 26-30, 34-36, 96-97 (made available to the public on Dec. 15, 1988)—Call No. "T3.6.L821987".
McNaught A.D., et al., "The Compendium of Chemical Terminology," The Gold Book, Second Edition, Blackwell Science, 1997.
Schultz J.S., et al., "Optical Fiber Affinity Sensors," Methods in Enzymology, K. Mosbach, Ed., Academic Press, 1988, vol. 137, pp. 349-366.
West, Electrodeposition and Corrosion Processes, 1971.
Wong CM., et al., "Glucose Oxidase: Natural Occurrence, Function, Properties and Industrial Applications," Applied Microbiology and Biotechnology, 2008, vol. 78 (6), pp. 927-938.
Morris C.G., Definition of "Machine Learning", Academic Press Dictionary of Science and Technology (4th ed.), 1992, Oxford, UK: Elsevier Science & Technology. Retrieved from https://search.credoreference.com/content/entry/apdst/machine_learning/0?institutionId=743.
Heraeus Technical Data Sheet, Thick Film Materials, Product CL11-5100, retrieved from the Internet on Jun. 14, 2019.
Heraeus Technical Data Sheet, Thick Film Materials, Product CL11-5349, retrieved from the Internet on Jun. 14, 2019.
Heraeus Technical Data Sheet, Thick Film Materials, Product CL11-6109, retrieved from the Internet on Jun. 14, 2019.
Heraeus Technical Data Sheet, Thick Film Materials, Product LP11-4493, retrieved from the Internet on Jun. 14, 2019.

\* cited by examiner
‡ imported from a related application

BIO-ADAPTABLE IMPLANTABLE SENSOR APPARATUS AND METHODS

GRANT INFORMATION

This invention was made in part with government support under NIH Grant No. DK-77254. The United States government has certain rights in this invention.

RELATED APPLICATIONS

This application is related to co-owned and co-pending U.S. patent application Ser. No. 13/559,475 filed Jul. 26, 2012 entitled "Tissue Implantable Sensor With Hermetically Sealed Housing," Ser. No. 14/982,346 filed Dec. 29, 2015 and entitled "Implantable Sensor Apparatus and Methods", and Ser. No. 15/170,571 filed Jun. 1, 2016 and entitled "Biocompatible Implantable Sensor Apparatus And Methods", each of the foregoing incorporated herein by reference in its entirety. This application is also related to U.S. patent application Ser. No. 10/719,541 filed Nov. 20, 2003, now issued as U.S. Pat. No. 7,336,984 and entitled "Membrane and Electrode Structure for Implantable Sensor," also incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

1. TECHNICAL FIELD

The disclosure relates generally to the field of sensors, therapy devices, implants and other devices which can be used consistent with human beings or other living entities for in vivo detection and measurement or delivery of various solutes, and in one exemplary aspect to methods and apparatus enabling the use of such sensors and/or electronic devices for, e.g. monitoring of one or more physiological parameters, including through use of a novel membrane structure and/or other components and characteristics.

2. DESCRIPTION OF RELATED TECHNOLOGY

Implantable electronics is a rapidly expanding discipline within the medical arts. Owing in part to great advances in electronics and wireless technology integration, miniaturization, performance, and material biocompatibility, sensors or other types of electronics which once were beyond the realm of reasonable use in vivo in a living subject can now be surgically implanted within such subjects with minimal effect on the recipient subject, and in fact many inherent benefits.

One particular area of note relates to blood glucose monitoring for subjects, including those with so-called "type 1" or "type 2" diabetes. As is well known, regulation of blood glucose is impaired in people with diabetes by: (1) the inability of the pancreas to adequately produce the glucose-regulating hormone insulin; (2) the insensitivity of various tissues that use insulin to take up glucose; or (3) a combination of both of these phenomena. Safe and effective correction of this dysregulation requires blood glucose monitoring.

Currently, glucose monitoring in the diabetic population is based largely on collecting blood by "fingersticking" and determining its glucose concentration by conventional assay. This procedure has several disadvantages, including: (1) the discomfort associated with the procedure, which should be performed repeatedly each day; (2) the near impossibility of sufficiently frequent sampling (some blood glucose excursions require sampling every 20 minutes, or more frequently, to accurately treat); and (3) the requirement that the user initiate blood collection, which precludes warning strategies that rely on automatic early detection. Using the extant fingersticking procedure, the frequent sampling regimen that would be most medically beneficial cannot be realistically expected of even the most committed patients, and automatic sampling, which would be especially useful during periods of sleep, is not available.

Implantable glucose sensors have long been considered as an alternative to intermittent monitoring of blood glucose levels by the fingerstick method of sample collection. These devices may be fully implanted, where all components of the system reside within the body and there are no through-the-skin (i.e. percutaneous) elements, or they may be partially implanted, where certain components reside within the body but are physically connected to additional components external to the body via one or more percutaneous elements. The operability of one such fully implanted sensor has been demonstrated as a central venous implant in dogs (Armour et al., Diabetes, 39:1519 1526 (1990), incorporated herein by reference in its entirety). Although this sensor provided direct recording of blood glucose, which is most advantageous for clinical applications, the described implantation at a central venous site poses several risks and drawbacks, including risk of blood clot formation and vascular wall damage. An alternative that does not present such risks to the user is to implant the sensor in a "solid" tissue site and to relate the resulting signal to blood glucose concentration.

Typical sensors implanted in solid tissue sites measure the concentration of solutes, such as glucose, in the blood perfusing the microcirculation in the vicinity of the sensor. Glucose diffuses from nearby capillaries to the sensor surface. Because such diffusion occurs effectively only over very small distances, the sensor responds to the substrate supply only from nearby blood vessels. Conversely, solutes that are generated in the locality of the sensor may be transported away from the sensor's immediate vicinity by the local microvasculature. In either case, access to and/or association with the local microcirculation may influence the sensor's response.

Optical glucose sensors are known in the prior art. Schultz and Mansouri disclosed one such version of an optical sensor (J. S. Schultz and S. Mansouri, "Optical Fiber Affinity Sensors," Methods in Enzymology, K. Mosbach, Ed., Academic Press, New York, 1988, vol. 137, pp. 349-366). A variety of other optical techniques including optical coherence tomography, near infrared spectroscopy, Raman spectroscopy, and polarimetry have been tried and failed. Light-based systems using either absorption of light, or emission of light when glucose is "excited" by light have not proven to be accurate since there is no specific light absorption or emission spectrum for glucose. Furthermore, numerous other chemicals or interfering substances in the blood overlap in spectrum with glucose, causing optical methods to be insufficiently specific for glucose monitoring.

A number of electrochemical glucose sensors have also been developed, most of which are based on the reaction catalyzed by the enzyme glucose oxidase. One such configuration involves the use of glucose oxidase to catalyze the reaction between glucose and oxygen to yield gluconate and hydrogen peroxide. The hydrogen peroxide is either detected directly, or can be further decomposed by a second enzyme, e.g. catalase, in which case the sensor measures oxygen consumption. In order for glucose oxidase based sensors to function properly, the presence, in the vicinity of the enzyme, of excess molecular oxygen relative to molecular glucose is necessary. However, this requirement gives rise to a sensor design problem related to "oxygen deficit," since the concentration of oxygen in bodily tissues is significantly less than that of glucose.

For example, the typical concentration of glucose in the blood is about 4 to about 20 mM, whereas a typical concentration of oxygen in blood plasma may be only about 0.05 to about 0.1 mM. Oxygen concentrations in other tissue fluids may be even lower. As the chemical reaction, and thus, the sensor signal, is limited by the reactant that is present in the sensor's reaction zone at the lowest concentration, an implanted sensor of simple construction would remain limited by oxygen, and would therefore be insensitive to the metabolite of interest (e.g. glucose). Thus, there is a need for differential control of the permeability of the sensor diffusion device (e.g., "membrane") to restrict or modulate the flux of the metabolite of interest (e.g. glucose), and provide a stoichiometric equivalent or excess of oxygen in the reaction zone. The sensor incorporating such a membrane can then be sensitive to the metabolite of interest over the physiologic range. Also, for successful functioning of the implanted sensor, the membrane material exposed to the bodily tissue must further be biocompatible, or elicit a favorable response from the body. Several membrane solutions have been proposed to date.

One such solution has been through the use of macroporous or microporous membranes to ratio the diffusion of oxygen and glucose to the sensing elements, such as that set forth in U.S. Pat. No. 4,759,828 to Young, which discloses use of a laminated membrane with an outer microporous membrane having a pore size of 10 to 125 A (Angstrom) to limit the diffusion of glucose molecules. However, one problem with the use of a macroporous or microporous membrane relates to exposure of the sensing element of the sensor to the environment of the body, which can result in "fouling" or other deleterious effects. Another solution is disclosed in U.S. Pat. No. 4,671,288 to Gough, which describes a cylindrical device, implantable in an artery or vein, which is permeable to glucose only at an end of the device, and with both the curved surface and end permeable to oxygen. In vascular applications, the advantage is direct access to blood glucose, leading to a relatively rapid response. However, a major disadvantage of vascular implantation is the possibility of eliciting blood clots or vascular wall damage, as noted supra.

U.S. Pat. No. 5,660,163 to Schulman discloses another solution through use of a silicone rubber membrane containing at least one "pocket" filled with glucose oxidase in a gelatinous glucose- and oxygen-permeable material located over a first working electrode, such that the length of the "pocket" is a multiple of its thickness to optimize the linearity between current and the glucose concentration measurement. However, because the long axis of the "pocket" is oriented parallel to the electrode surface, this design may be less amenable to miniaturization for tissue implantation, and may suffer from yet other disabilities relating thereto.

Still further, another solution has been to utilize a composite membrane that is hydrophilic and also contains small hydrophobic domains to increase the membrane's overall gas solubility, giving rise to differential permeability of glucose and oxygen (e.g. U.S. Pat. Nos. 4,484,987 and 4,890,620 to Gough). However, one salient disadvantage of this approach relates to the requirement that the amount of hydrophobic polymer phase must be relatively large to allow for adequate oxygen permeability. This substantially reduces the hydrophilic volume available for enzyme inclusion sufficient to counter inactivation during long-term operation.

Another alternative is described in U.S. Pat. No. 4,650,547 to Gough, which discloses a "stratified" structure in which the electrode was first overlaid with an enzyme-containing layer, and second with a non-glucose-permeable membrane. The resulting structure is permeable to oxygen over a large portion of the surface of the membrane, whereas glucose can only reach the enzyme through the "edge" of the device, thus regulating access of the reactants to the enzyme.

A significant concern in the context of e.g., implantable solid tissue devices is the so-called "tissue response", wherein the host's physiology proximate to the implanted sensor is irritated or adversely stimulated into an antibody-modulated or other response which can be deleterious to the operation of the implanted device, especially over longer periods of time. The process of implantation (i.e., creation of a wound) and the presence of a device (i.e., a foreign body) within living tissue cause early host reactions (e.g., within two to four weeks of implantation) that generally include: (i) blood-biomaterial interaction, (ii) provisional matrix formation, (iii) acute inflammation, (iv) chronic inflammation, (v) foreign body reaction (FBR), and (vi) fibrosis/fibrous capsule development (Anderson, James. "Biological Responses to Materials." *Annu. Rev. Mater. Res.* 31(2001): 81-110.). Each of these phases of wound healing has a cascade effect, including release of specific bio-chemicals (e.g., mitogens, chemoattractants, cytokines, growth factors, etc.) and migration of specific wound healing-associated cells (e.g., neutrophils, macrophages, fibroblasts, foreign body giant cells, etc.) to the implant site, which leads to subsequent phases, and eventually adaptation to or rejection of the implanted device.

In some cases, although the living tissue adapts to the implanted device, the wound healing process may render the device non-functional (or at very least reduce its functionality and/or accuracy), thereby negating any benefit to the patient. For example, in implanted devices that depend on diffusive transport of solutes to or from the bloodstream (e.g. implanted chemical sensors), such responses can negatively impact device operation due to an increase in mass transfer resistance between the bloodstream and active portions of the device surface resulting from an FBR-mediated development of fibrous tissue surrounding the device. The FBR also can complicate explants of the implanted device (due to, e.g., the FBR causing significant encapsulation of the implanted device, thereby increasing its effective size when explanted), and result in yet other disabilities. Thus, accounting for (and minimizing) the FBR remains an important consideration for nearly all implanted devices. Some prior art solutions for implantable sensors have attempted to use layers external to the sensing enzyme region to actively modulate or eliminate the FBR. Such approaches have typically used materials for such layer(s) which are designed to encourage blood vessel growth and perfusion in the vicinity of the sensor or into the layer(s), which is undesirable, because such modulated responses are often not predictable and furthermore may not be sustainable for extended durations.

An illustration of the final phases of a typical wound healing 100 response are depicted in the example of FIG. 1, showing an implanted object 102 and surrounding host tissue 104. In the FBR phase 106 of wound healing, tissue repair cells 108 (e.g., macrophages, foreign body giant cells, etc.) are recruited to the surface of the object 102 and the surrounding tissue 104. Subsequently, in the fibrosis phase 110, the object 102 undergoes fibrous encapsulation by granulation tissue and/or connective tissue 112.

Biocompatibility of a medical device, such as e.g., an implantable sensor, may be defined as the ability of the device to perform as intended with an appropriate host wound healing response, while minimizing the magnitude and duration of the wound healing response. Factors that affect biocompatibility may include, inter alia, extent of injury (e.g., amount of tissue removal, size of incision, etc.) resulting from the implantation process, integrity of basement membrane structures during and after implantation, material compositions of the device, surface properties of the device, dimensions of the device, exposure of tissues to electrical and/or chemical components (including byproducts) of the device, motion and/or migration of the device in the implant site, and ability to function under at least a minimal degree of granulation tissue formation, FBR, and fibrosis.

Traditionally, "solid tissue" sensors (including the aforementioned glucose sensors) are implanted within the living subject at a generally superficial layer or level of the tissue, so as to (i) mitigate tissue trauma resulting from the surgical implantation procedure, and (ii) mitigate interference from interposed solid tissue to the propagation of electromagnetic radiation (e.g., wireless transmissions to and from the implant). Specifically, historically larger implants require a larger volume within the solid tissue of the recipient, and hence placing the larger implant further down into the layers of tissue, etc. residing below the epidermis requires a larger incision, possibly including through various blood vessels, basement membranes, and/or other features and possibly requiring removal of some solid tissue to accommodate the volume of the implant, thereby likely extending duration and intensity the host's wound healing response.

Further, some sensors may expose the host tissue to harmful chemicals or compounds that increase perturbation of host tissue and reaction of the tissue to the implant. In one specific example, some conventional glucose sensors monitor glucose via detection of hydrogen peroxide, which is a product of glucose reaction with oxygen catalyzed by the glucose oxidase (GOx) enzyme. Hydrogen peroxide is widely regarded as a cytotoxic agent that can lead to cell death and tissue necrosis in excess concentrations, both of which stimulate the wound healing response. In another example, some glucose sensors (peroxide-based or otherwise) may be configured such that enzyme-embedded membranes are directly exposed to the host blood and tissue, which may trigger an immunogenic response. In even another example, some implants may be comprised of materials that increase duration and/or intensity of wound healing.

Likewise, electrical circuitry and/or electrochemical processes associated with an implanted or partly implanted device may trigger a similar immunogenic response in the host. For instance, electrical currents and potentials associated with an electrolytic sensor can, if sufficiently proximate to the host's tissue, induce varying degrees of the aforementioned tissue response, which is likewise undesired.

Additionally, motion and/or migration of an implanted device may exacerbate the chronic inflammation phase of wound healing. Prolonged chronic inflammation is also associated with increased FBR and fibrosis, and may lead to implant rejection and require extraction or "explant" (i.e., removal of the sensor). The explant process generally becomes more difficult and traumatic to the tissue if there is significant FBR and fibrosis, which may cause tissue to responsively grow connective tissue around the implanted sensor over time.

It is recognized that at least minimal levels of FBR and fibrosis (i.e., end stages of tissue response) are normal to the wound healing process. The FBR is characterized by the formation of foreign body giant cells, which adhere to surfaces of the device and stimulate fibrosis (i.e., encapsulation by fibrous connective tissue with a decreased density of capillary blood vessels relative to undisturbed tissue) of the device in an attempt to isolate the implant and FBR from the local tissue environment. The materials, form, and topography of the surface of the implanted device, as well as the degree and duration of previous stages of wound healing may all effect the FBR and fibrosis processes. When the FBR is minimized, there is generally increased regeneration of normal tissue, and replacement of tissue by the fibrous capsule is decreased. In some conventional implanted sensors, even normal degrees of FBR and fibrosis may obstruct the sensing components, thereby rendering the device non-functional and necessitating replacement (i.e., explant of the current device and implant of a new device), which may reinitiate the wound healing process.

Moreover, blood vessel vascularization and "ingrowth" into portions of an implanted device (such as an implanted sensor) may occur in certain prior art applications, effectively bonding the device (at least in certain areas) to the host, thereby precluding a clean separation of the device from the surrounding FBR-induced encapsulation during device explant. Some prior art solutions for implantable sensors have attempted to use layers external to the sensing enzyme region to actively modulate or eliminate the FBR; see, e.g., U.S. Pat. No. 6,558,321 to Burd, et al. entitled "Systems and methods for remote monitoring and modulation of medical devices," which describes use of a porous material on the exterior of the sensor's enzyme membrane element. Such approaches have typically used materials for such layer(s) which are designed to encourage blood vessel growth and perfusion in the vicinity of the sensor or into the layer(s), which is undesirable, because such modulated responses are often not predictable and furthermore may not be sustainable for extended durations.

Accuracy is also an important consideration for implanted analyte sensors, especially in the context of blood glucose monitoring. Hence, ensuring accurate measurement for extended periods of time (and minimizing the need for any other confirmatory or similar analyses) is of great significance. The response and accuracy of conventional sensors can be adversely affected by FBR or other tissue response in the region of the analyte sensor as noted above; this effect can be exacerbated the longer the sensor is left implanted. Specifically, as the FBR or tissue response proceeds over time, the mechanical relationship between an implanted sensor device and the host's tissue in the immediate area of implantation (including micro-perfusion within blood vessels adjacent to the sensor) can significantly change due to movement between the tissue (and the microvascular structures therein which provide communication between the device and the body's circulatory system) and the device surface, thereby potentially degrading the accuracy and/or reliability of the sensor device. Notwithstanding, the host tissue needs to be maintained in close physical contact with the detector or sensor of the implanted device, in order for the sensor to operate properly (e.g., the blood glucose molecules to migrate into the sensor for utilization therein). Hence, there is somewhat of a "catch-22" involved; any effective sensor will need to be implanted at a site with sufficient available blood glucose (delivered via blood vessels or microvasculature of the host in that area) and maintain close physical contact with the tissue at that site for proper and accurate sensor operation, yet such close contact (including even the act of implantation) can trigger a tissue response which can be deleterious to the accuracy and operation of the sensor. Sensors relying on the diffusion of glucose are particularly susceptible to variations in tissue response and encapsulation, since these factors directly affect the rate and magnitude of glucose diffusion from the capillaries to the implanted sensor element.

Lastly, many conventional implantable devices are sufficient only for relatively short-term implantation due to expiration or exhaustion of one or more components of the device (as well as the aforementioned degradation of accuracy/response due to effects of the FBR). In this case, similar to devices obstructed by FBR and fibrosis, the devices may necessitate frequent replacement (i.e., explant of the current device and implant of a new device), which may reinitiate the wound healing process.

As such, there is a compelling need for an implantable biocompatible analyte sensor designed to operate accurately over extended periods of implantation, while decreasing the duration and/or intensity of wound healing responses from the host (including biocompatibility features that avoid the foregoing disabilities and drawbacks associated with prior art implantable devices), as well as techniques for operating the sensor so as to enhance its performance and longevity/viability within the host being.

SUMMARY

The present disclosure satisfies the foregoing needs by providing, inter alia, improved implantable apparatus for accurately sensing analyte levels within a living subject, including for extended periods of time without explant, and methods of operating the same.

In one aspect, an implantable analyte sensor is disclosed. In one embodiment, the sensor includes: a biocompatible housing having a size and shape suitable for implantation in a body; a plurality of analyte detectors; circuitry operatively connected to the plurality of detectors and configured to process at least a portion of signals generated by one or more of the detectors to produce processed signals; data transmission apparatus configured to transmit at least a portion of the processed signals to a receiver (whether inside the body, outside of the body, or combinations thereof) when the implanted sensor is disposed in a tissue environment within the body; and an electrical power source operatively coupled to at least the circuitry and data transmission apparatus and configured to provide electrical power thereto. In one variant, the sensor further comprises apparatus configured to promote interlock of at least a portion of the plurality of detectors with biological tissue of the body proximate thereto without substantive blood vessel ingrowth.

In one implementation, the analyte comprises blood glucose, and the apparatus configured to promote interlock comprises at least one membrane configured for direct contact with the biological tissue after implantation of the sensor, the at least one membrane at least partly permeable to diffusion of the blood glucose therethrough, yet which is configured to frustrate the blood vessel ingrowth.

In another embodiment, the sensor includes: a biocompatible housing having a size and shape suitable for implantation in a body; a plurality of analyte detectors; circuitry operatively connected to the plurality of detectors and configured to process at least a portion of signals generated by one or more of the detectors to produce processed signals; data transmission apparatus configured to transmit at least a portion of the processed signals to a receiver when the implanted sensor is disposed in a tissue environment within the body; and an electrical power source operatively coupled to at least the circuitry and data transmission apparatus and configured to provide electrical power thereto. The sensor is configured to not stimulate blood vessel vascularization at least proximate to the plurality of detectors, yet permit diffusion of the analyte (e.g., glucose) into the plurality of detectors.

In yet another embodiment, the sensor includes: a biocompatible housing having a size and shape suitable for implantation in a body; a plurality of analyte detectors; circuitry operatively connected to the plurality of detectors and configured to process at least a portion of signals generated by one or more of the detectors to produce processed signals; data transmission apparatus configured to transmit at least a portion of the processed signals to a receiver when the implanted sensor is disposed in a tissue environment within the body; and an electrical power source operatively coupled to at least the circuitry and data transmission apparatus and configured to provide electrical power thereto. The circuitry is configured such that at least a portion of the plurality of detectors are able to adapt for variations in a biophysical interface between the detectors and biological tissue of the body over time, the variations caused at least in part by biological processes within the body.

In another aspect, a method of configuring an implantable sensing device so as to limit tissue response from a living host in which the device is ultimately implanted is disclosed. In one embodiment, the method includes configuring the sensing device to facilitate contact of at least one outer membrane thereof with tissue of the living host when the device is implanted, the facilitating contact comprising (i) enabling tissue response by the living host to substantially cover or encase at least a portion of the at least one outer membrane; and (ii) not encouraging or avoiding vascularization by the living host into the at least one outer membrane.

In one variant, the implantable sensor comprises a glucose sensor, and the enabling tissue response comprises configuring the sensing device such that it is in direct physical contact with the tissue of the living host when implanted so as to facilitate migration of at least blood glucose molecules to the at least one outer membrane, and the not encouraging vascularization comprises configuring the at least one outer membrane to have a pore size on at least an outer surface thereof sufficient to inhibit the vascularization.

In another aspect, a method of maintaining a position and orientation of an implantable sensor within a living host while also maintaining its operability is disclosed. In one embodiment, the sensor includes a sensing feature for sensing an analyte (e.g., glucose), and the method includes: implanting the sensor within a location of the host; enabling a tissue response to the implanted sensor such that tissue of the host proximate the implanted sensor substantially interlocks with the sensing feature; and frustrating vascularization of the tissue into the sensing feature. The substantial interlock with the sensing feature provides mechanical stability to the sensor so as to maintain the position and orientation, minimizing movement between the sensor surface and the tissue adjacent to the sensor without causing any significant "bonding" of the tissue to the sensing feature or sensor body. Minimizing the potential for relative movement or slippage between the sensor surface and the adjacent tissue helps ensure stability of the sensor response characteristics and also avoids exacerbating the FBR from mechanically-induced fibrotic response effects.

In another aspect, a miniaturized biocompatible implantable sensor is disclosed. In one embodiment, the sensor comprises a plurality of oxygen-based glucose sensing elements disposed on a sensing region thereof, and is fabricated from biocompatible materials and uses biocompatible processes for sensing which advantageously mitigate or eliminate physiological responses from the host (e.g., chronic inflammation, FBR, blood vessel in-growth, and/or fibrosis), while also enabling close physical contact with the host's tissue so as to permit long-term, accurate blood glucose monitoring and easy subsequent explant of the sensor.

In one variant, the sensor is further configured to dynamically accommodate any tissue changes which do occur, algorithmically (e.g., within the control logic of the device). In one particular implementation, the miniaturized size, optimized materials and construction, and adaptive operation of the sensor apparatus enable, inter alia, deeper and less traumatic implantation within the host's solid tissue (and subsequent extraction) and continued operation within the host for extended periods of time, thereby providing all of the benefits of an implantable sensor without the attendant disabilities of both prior art implantable devices and associated techniques.

In a further aspect, a method of extending the in vivo operating lifetime of an implantable electronic device is disclosed. In one embodiment, the method includes controlling a level of tissue response and blood vessel vascularization from a host being over time such that close contact between the solid tissue of the host and a sensing region of the implantable device is achieved, yet simultaneously mitigating vascularization into the sensing region and encapsulation of at least the remainder of the sensing apparatus. In one variant, the foregoing control is accomplished via coordination of a plurality of configuration factors, including: (i) electrical insulation of the solid tissue in at least the sensing region of the device, (ii) enzyme insulation of the solid tissue in at least the sensing region of the device; (iii) use of an outer anti-vascularization sensor barrier for at least some of the sensors in the sensing region, and (iv) use of substantially smooth, biocompatible materials for portions of the device outside of the sensing region.

In yet another aspect, a method of implantation is disclosed. In one embodiment, the method includes implanting a sensor apparatus having a sensing region configuration in a living subject so as to mitigate FBR and adhesion of the tissue to the sensing region, and create a topological "imprint" in three dimensions, and then subsequently explanting the sensor apparatus and implanting a replacement sensor apparatus (or the explanted apparatus that has been refitted or refurbished) with the same or similar sensing region configuration in the same location, and utilizing the same imprint for the sensing region thereof.

In a further aspect, a surgical method is disclosed. In one embodiment, the method includes: implanting a sensor apparatus having a sensing region configuration in a living subject, the sensor apparatus configured to mitigate adhesion of the tissue to the sensing region resulting from a body response; and substantially immobilizing the sensor apparatus within the living subject as part of the implanting. In one implementation, the implanting and immobilizing enable creation of a topological imprint feature in three dimensions, the imprint feature and the mitigated adhesion cooperating to enable subsequent explanting of the sensor apparatus and implanting a replacement sensor apparatus having a substantially similar sensing region configuration utilizing the same imprint feature for the sensing region thereof.

Other features and advantages of the present disclosure will immediately be recognized by persons of ordinary skill in the art with reference to the attached drawings and detailed description of exemplary embodiments as given below.

BRIEF DESCRIPTION OF THE DRAWINGS

FIGS. 2A-2C are top, bottom, and side elevation views, respectively, of the exemplary sensor apparatus of FIG. 2.

Figure 1:
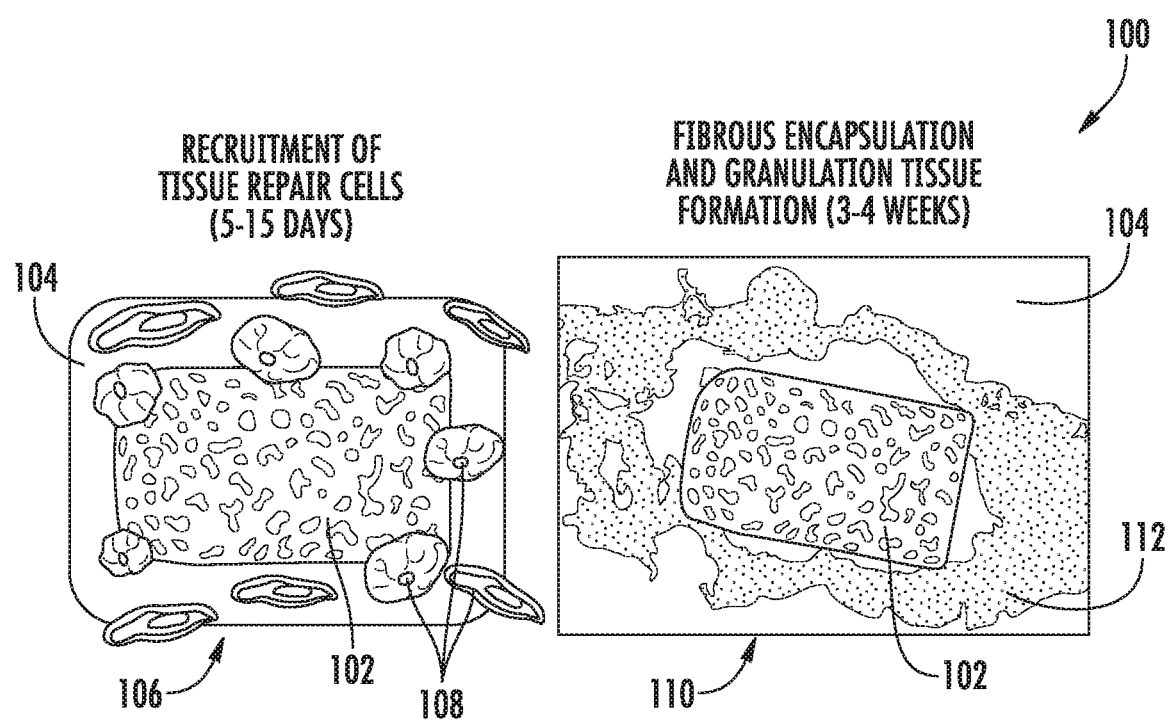
FIG. 1 is an illustration of foreign body response and fibrosis phases of a typical wound healing response that may occur after implantation of an object or device.

All Figures © Copyright 2015-2016 GlySens Incorporated. All rights reserved.

DETAILED DESCRIPTION

Reference is now made to the drawings, wherein like numerals refer to like parts throughout.

Overview

In one exemplary aspect, the present disclosure provides a fully-implantable sensor apparatus that is particularly adapted to both utilize and mitigate tissue response, thereby enabling accurate in vivo operation over long durations. It is recognized by the inventors hereof that such tissue response cannot be completely eliminated; hence, the methods and apparatus of the present disclosure make advantageous use of the tissue response (i.e., to promote a high degree of stable contact with a sensing region of the sensor apparatus—in effect creating an "imprint" of the sensing region on the host's tissue), yet also simultaneously mitigate unwanted tissue response including vascularization and significant encapsulation, each of which can adversely impact the operation of the sensor apparatus over time, and make the sensor apparatus difficult to explant (and hence create more tissue trauma within the host).

In one variant, the sensor apparatus is a miniaturized somewhat planar oxygen-based, biocompatible glucose sensor with multiple (e.g., 8) individual sensor elements disposed in a common sensing region on one side of the housing. The apparatus may be implanted within the host's torso (e.g., subcutaneous and proximate to the extant abdominal muscle fascia), and oriented so that the sensing region faces away from the skin surface (e.g., the plane of the sensor is substantially parallel to the fascia and the epidermis/dermis, with the sensing region facing inward toward the musculature under the fascia) and in direct contact with the solid tissue of the host, for inter alia close contact with blood-rich tissues and substantial mechanical stability.

The sensor apparatus include biocompatibility features that limit or mitigate the host tissue response to implantation and the presence of the foreign body within the host for extended periods. In one implementation, these features include: (i) use of a low-porosity non-enzymatic membrane over each of the individual sensor elements or detectors so as to preclude contact of the surrounding host solid tissue with the underlying enzyme matrix (and also potentially between the host tissue and reaction byproducts), and simultaneously frustrate or eliminate vascularization; (ii) insulation of the various electrodes and associated electrochemical processes of the sensor from the surrounding host solid tissue so as to mitigate any tissue response due to electrical currents or potentials generated by the individual detectors; (iii) use of a non-agitating (e.g., non-peroxide) based enzyme matrix material for analyte detection; (iv) use of biocompatible materials for the housing and other components of the sensor apparatus; (v) use of anti-migration features such as anchors or tethers, as well as the shape and implantation placement of the device; and/or (vi) reduction of the size of the implanted apparatus.

Concurrently, the sensor region of the apparatus is sized and shaped to facilitate a high degree of contact with blood-carrying solid tissue of the host at the implantation site, thereby facilitating ready (and consistent) migration of blood glucose molecules into the individual detectors of the sensor apparatus, and promoting physical interlock with the solid tissue (and subsequent tissue response) of the host.

In practice, the exemplary sensor apparatus provides excellent and reliable contact (and hence analyte migration and subsequent sensing) with the host's solid tissue at the implantation site, yet avoids vascularization and its attendant problems, and avoids exacerbating fibrous encapsulation of the apparatus, thereby facilitating longer-term operation in vivo, and easier (and less traumatic) subsequent explant.

The exemplary implementation of the foregoing biocompatible sensor apparatus is also advantageously suitable for "long-term" implantation (e.g., 12-18 months) by virtue of its design and operation, thereby decreasing reoccurrence of injury and repeated inducement of the wound healing response necessitated by expiration and replacement of the device, which can be performed on an outpatient basis by a clinician using only local anesthetic and recovery time from the procedure is minimal.

Moreover, the foregoing imprint created by the sensor apparatus can be advantageously re-used (whether by a subsequent replacement sensor of the same or similar configuration, or the same sensor apparatus that has been e.g., refitted with a new battery), so that the foreign body response or other deleterious host responses are yet further avoided, and trauma to the host is minimized.

The aforementioned implementation may include one or more features that dynamically adapt operation of the sensor apparatus to the host's tissue response over time, leveraging the observation that any non-mitigated response can be accounted for by the sensor apparatus, such as via signal processing either within, or off-board from, the sensor apparatus while implanted.

DETAILED DESCRIPTION OF EXEMPLARY EMBODIMENTS

Exemplary embodiments of the present disclosure are now described in detail. While these embodiments are primarily discussed in the context of a fully implantable glucose sensor, such as those exemplary embodiments described herein, and/or those set forth in U.S. Pat. No. 7,894,870 to Lucisano et al. issued Feb. 22, 2011 and entitled "Hermetic implantable sensor;" U.S. Patent Application Publication No. 20110137142 to Lucisano et al. published Jun. 9, 2011 and entitled "Hermetic Implantable Sensor;" U.S. Pat. No. 8,763,245 to Lucisano et al. issued Jul. 1, 2014 and entitled "Hermetic feedthrough assembly for ceramic body;" U.S. Patent Application Publication No. 20140309510 to Lucisano et al. published Oct. 16, 2014 and entitled "Hermetic Feedthrough Assembly for Ceramic Body;" U.S. Pat. No. 7,248,912 to Gough, et al. issued Jul. 24, 2007 and entitled "Tissue implantable sensors for measurement of blood solutes;" U.S. Pat. No. 7,871,456 to Gough et al. issued Jan. 18, 2011 and entitled "Membranes with controlled permeability to polar and apolar molecules in solution and methods of making same;" and U.S. Patent Application Publication No. 20130197332 to Lucisano et al. published Aug. 1, 2013 and entitled "Tissue implantable sensor with hermetically sealed housing;" PCT Patent Application Publication No. 2013016573 to Lucisano et al. published Jan. 31, 2013 and entitled "Tissue implantable sensor with hermetically sealed housing," each of the foregoing incorporated herein by reference in its entirety, it will be recognized by those of ordinary skill that the present disclosure is not so limited. In fact, the various aspects of the disclosure are useful with, inter alia, other types of implantable sensors and/or electronic devices.

Further, while the following embodiments describe specific implementations of e.g., biocompatible oxygen-based multi-sensor element devices, and specific protocols, locations and orientations for implantation (e.g., proximate the waistline on a human abdomen with the sensor array disposed proximate to fascial tissue; see e.g., U.S. patent application Ser. No. 14/982,346 filed Dec. 29, 2015 and entitled "Implantable Sensor Apparatus and Methods" previously incorporated herein), those of ordinary skill in the related arts will readily appreciate that such descriptions are purely illustrative, and in fact certain aspects of the methods and apparatus described herein may be used consistent with, and without limitation: (i) other implantation locations and/or techniques; (ii) living beings other than humans; (iii) other types or configurations of sensors (e.g., peroxide-based glucose sensors, or sensors other than glucose sensors, such as e.g., for other analytes such as urea or lactate); and/or (iv) devices intended to deliver substances to the body (e.g. implanted drug pumps, drug-eluting solid materials, and encapsulated cell-based implants, etc.); and/or yet other devices (e.g., non-sensors and non-substance delivery devices).

As used herein, the terms "wound healing" and "tissue response" refer without limitation to biological processes that occur within a host or patient during and after implantation. The biological processes generally including the following phases: (i) blood-biomaterial interaction, (ii) provisional matrix formation, (iii) acute inflammation, (iv) chronic inflammation, (v) foreign body reaction (FBR), and (vi) fibrosis/fibrous capsule development. Although each phase is generally subsequent the preceding phase, phases maybe overlapping and/or reoccurring.

As used herein, the term "biocompatibility" refers without limitation to the ability of a medical device or implantable material to perform as intended in the presence of an appropriate host wound healing response and/or other immunogenic responses, while minimizing magnitude and duration of the wound healing (e.g., acute inflammation, chronic inflammation, foreign body reaction (FBR), and fibrosis/fibrous capsule development) and causing no significant harm to the patient.

As used herein, the terms "health care provider" and "clinician" refer without limitation to providers of health care services such as surgical procedures, diagnosis, monitoring, administration of pharmacological agents, counseling, etc., and include for instance physicians, nurses, medical assistants, technicians, and can even include the user/patient themselves (such as where the patient self-administers, self-monitors, etc.).

As used herein, the terms "orient," "orientation," and "position" refer, without limitation, to any spatial disposition of a device and/or any of its components relative to another object or being, and in no way connote an absolute frame of reference.

Likewise, as used herein, the terms "top," "bottom," "side," "up," "down," and the like merely connote, without limitation, a relative position or geometry of one component to another, and in no way connote an absolute frame of reference or any required orientation. For example, a "top" portion of a component may actually reside below a "bottom" portion when the component is mounted to another device or object.

As used herein, the terms "detector" and "sensor" refer without limitation to a device that generates, or can be made to generate, a signal indicative of a measured parameter, such as the concentration of an analyte (e.g., glucose or oxygen). Such a device may be based on electrochemical, electrical, optical, mechanical, thermal, or other principles as generally known in the art. Such a device may consist of one or more components, including for example, one, two, three, or four electrodes, and may further incorporate immobilized enzymes or other biological or physical components, such as membranes, to provide or enhance sensitivity or specificity for the analyte.

As used herein the term "membrane" refers without limitation to a substance, layer or element configured to have at least one desired property relative to the aforementioned analyte, such as e.g., a permeability to a given type of analyte or other substance.

As used herein, the terms "enzyme free" and "non-enzymatic" include, without limitation, materials that are completely enzyme-free, and materials that are substantially enzyme free (e.g., may have a small percentage of residual or unintentional enzymes).

Exemplary Implantable Sensor

Figure 2:
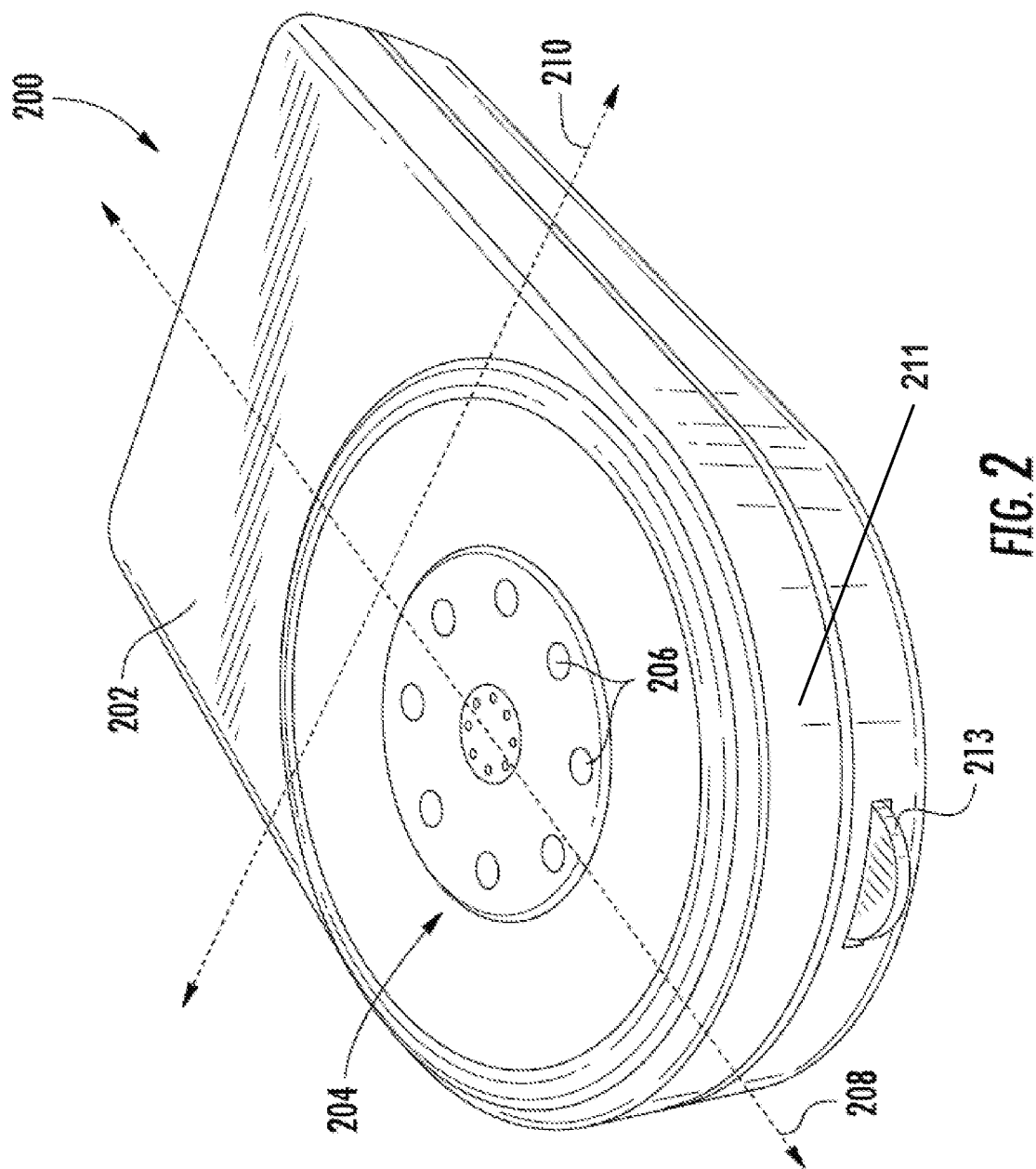
FIG. 2 is a front perspective view of one exemplary embodiment of a fully implantable biocompatible sensor apparatus according to the present disclosure.

Referring now to FIGS. 2-2C, one exemplary embodiment of a sensor apparatus useful with various aspects of the present disclosure is shown and described.

Figure 4:
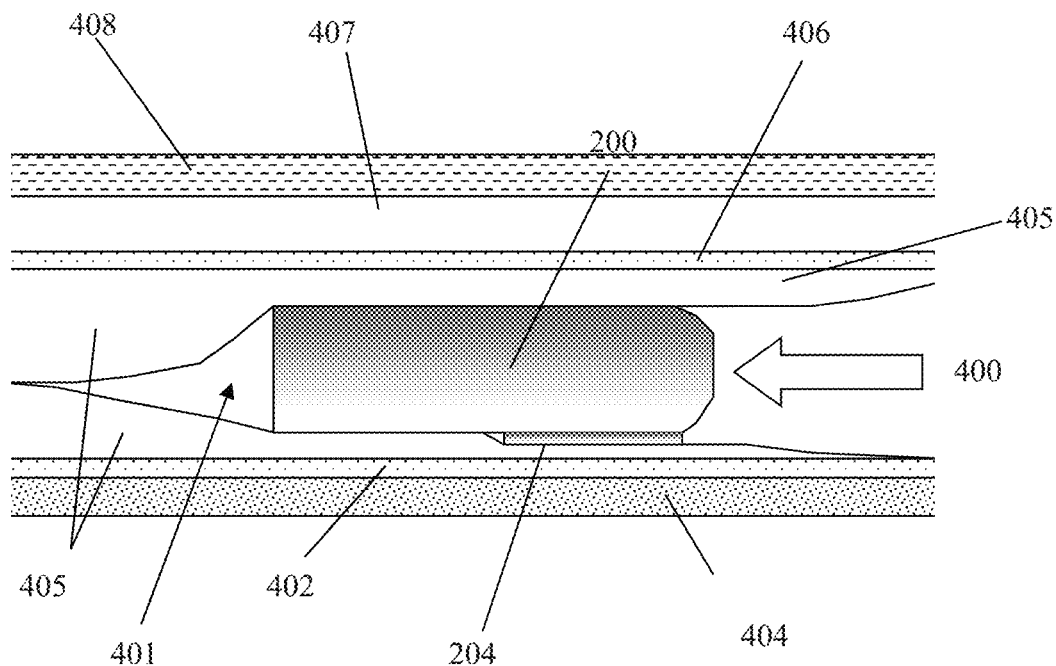
FIG. 4 is side cross-sectional view of an exemplary sensor apparatus implanted within a cavity or pocket formed in the tissue of the host, and proximate to the muscular fascia thereof.

As shown in FIGS. 2-2C, the exemplary sensor apparatus 200 comprises a somewhat planar housing structure 202 with a sensing region 204 disposed on one side thereof (i.e., a top face 202a). As described in greater detail below with respect to FIGS. 4-5, the exemplary substantially planar shape of the housing 202 provides mechanical stability for the sensor apparatus 200 after implantation, thereby helping to preserve the orientation of the apparatus 200 and mitigate any tissue response induced by movement of the apparatus while implanted. Notwithstanding, the present disclosure contemplates sensor apparatus of shapes and/or sizes other than that of the exemplary apparatus 200.

The sensor apparatus of FIGS. 2-2C further includes a plurality of individual sensor elements 206 with their active surfaces disposed substantially within the sensing region 204 on the top face 202a of the apparatus housing. In the exemplary embodiment (i.e., an oxygen-based glucose sensor), the eight (8) sensing elements 206 are grouped into four pairs, one element of each pair an active or "primary" sensor with enzyme matrix, and the other a reference or "secondary" (oxygen) sensor. Exemplary implementations of the sensing elements and their supporting circuitry and components are described in, inter alia, U.S. Pat. No. 7,248,912, previously incorporated herein. It will be appreciated, however, that the type and operation of the sensor apparatus may vary; i.e., other types of sensor elements/sensor apparatus, configurations, and signal processing techniques thereof may be used consistent with the various aspects of the present disclosure, including, for example, signal processing techniques based on various combinations of signals from individual elements in the otherwise spatially-defined sensing elements pairs.

As discussed in greater detail below with respect to FIG. 5, the illustrated embodiment of FIGS. 2-2C includes a sensing region 204 which facilitates some degree of "interlock" of the surrounding tissue (and any subsequent tissue response generated by the host) so as to ensure direct and sustained contact between the sensing region 204 and the blood vessels of the surrounding tissue during the entire term of implantation (as well as advantageously maintaining contact between the sensing region 204 and the same tissue; i.e., without significant relative motion between the two).

The sensor apparatus 200 also includes in the exemplary embodiment a wireless radio frequency transmitter (or transceiver, depending if signals are intended to be received by the apparatus), not shown. As described in the aforementioned documents incorporated herein, the transmitter/transceiver may be configured to transmit modulated radio frequency signals to an external receiver/transceiver, such as a dedicated receiver device, or alternatively a properly equipped consumer electronic device such as a smartphone or tablet computer. Moreover, the sensor apparatus 200 may be configured to transmit signals to (whether in conjunction with the aforementioned external receiver, or in the alternative) an at least partly implanted or in vivo receiving device, such as an implanted pump or other medication or substance delivery system (e.g., an insulin pump or dispensing apparatus), embedded "logging" device, or other. It is also appreciated that other forms of wireless communication may be used for such applications, including for example inductive (electromagnetic induction) based systems, or even those based on capacitance or electric fields, or even optical (e.g., infrared) systems where a sufficiently clear path of transmission and reception exists, such as two devices in immediately adjacent disposition.

The sensor apparatus of FIGS. 2-2C also includes a plurality (three in this instance) of tabs or anchor apparatus 213 disposed substantially peripheral on the apparatus housing. These anchor apparatus provide the implanting surgeon with the opportunity to anchor the apparatus to the anatomy of the living subject, so as to frustrate translation and/or rotation of the sensor apparatus 200 within the subject immediately after implantation but before any tissue response (e.g., FBR) of the subject has a chance to immobilize (such as via interlock with the sensing region of the apparatus. See e.g., U.S. patent application Ser. No. 14/982, 346 filed Dec. 29, 2015 and entitled "Implantable Sensor Apparatus and Methods" previously incorporated herein, for additional details and considerations regarding the aforementioned anchor apparatus 213 (which may include, for example features to receive sutures (dissolvable or otherwise), tissue ingrowth structures, and/or the like).

Figures 3, 3A:
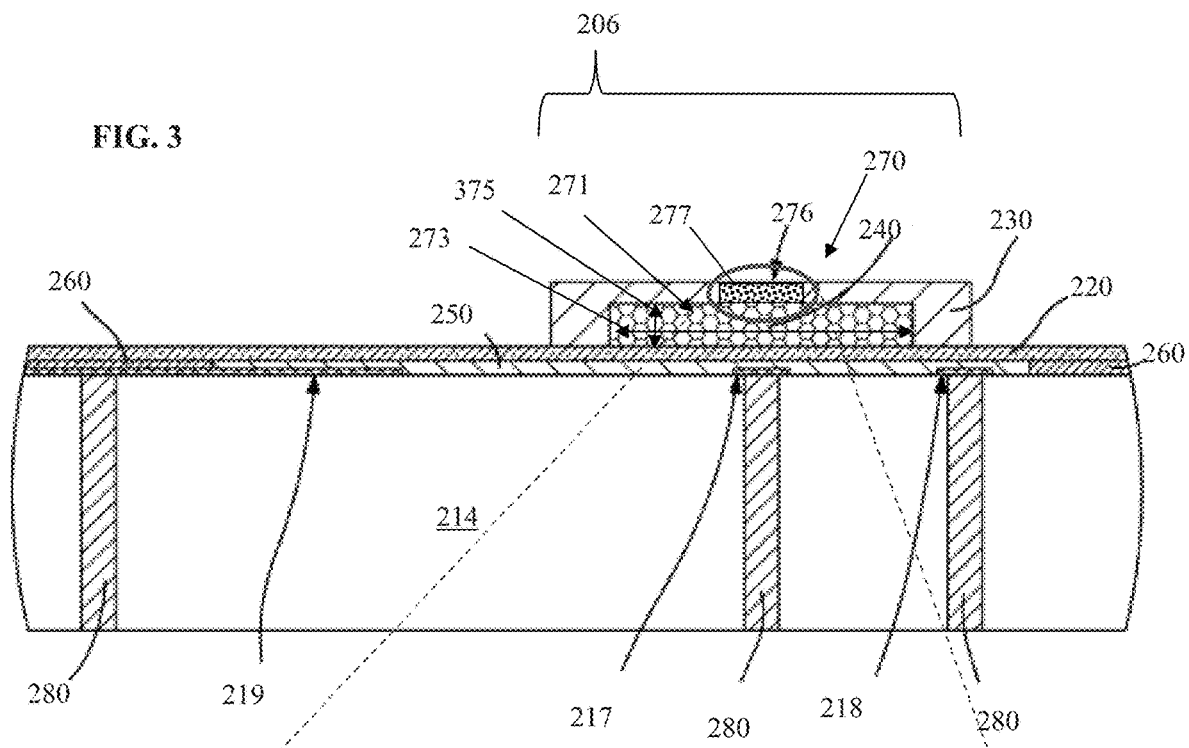
FIG. 3 is a side cross-sectional view of one exemplary detector element of a detector array in a fully implantable sensor apparatus according to the present disclosure.
FIG. 3A is a side cross-sectional view of one exemplary spout region (outer non-enzyme membrane removed) of a detector element of a detector array in a fully implantable sensor apparatus according to one embodiment of the present disclosure.

As shown in FIG. 3, an exemplary individual detector element 206 according to the present disclosure is shown associated with detector substrate 214 (e.g. ceramic substrate), and generally comprises a plurality of membranes and/or layers, including e.g., the insulating layer 260, and electrolyte layer 250, an enzymatic gel matrix of the type described above 240, an inner membrane 220, an exterior membrane shell 230, and a non-enzymatic membrane 277. Such membranes and layers are associated with the structure of individual detector elements, although certain membrane layers can be disposed in a continuous fashion across the entire detector array surface or portions thereof that include multiple detectors, such as for economies of scale (e.g., when multiple detectors are fabricated simultaneously), or for maintaining consistency between the individual detector elements by virtue of making their constituent components as identical as possible.

Generally, the thickness of each of the membranes disclosed herein is not particularly limited, as long as the desired permeability properties are achieved. However, particular requirements for sensor response time, glucose concentration detection range, and/or reduction of antibody response (e.g., FBR), may impose limits on the allowable membrane thickness. Membrane thickness can be, for example, about 1 micron to about 1000 microns, or more particularly, about 10 microns to about 500 microns, or more particularly about 25 microns to about 250 microns in certain applications. Very thin membrane layers, particularly those less than about 10 microns, may require mechanical support to be provided in the form of a backing membrane, which may be a porous, relatively inert structure. U.S. Pat. No. 7,336,984 and entitled "Membrane and Electrode Structure for Implantable Sensor," previously incorporated herein, describes exemplary membrane apparatus, thickness values, and computerized modeling techniques useful with the various aspects of the present disclosure, although it will be recognized that other techniques, apparatus, and methods for membrane configuration may be used consistent with the present disclosure.

As shown in FIGS. 3 and 3A, the detector elements 206 each further comprise a working electrode 217 in operative contact (by means of the electrolyte layer 250) with a counter electrode 219 and a reference electrode 218, and their associated feedthroughs 280 (details of the exemplary feedthroughs 380 are described in U.S. Pat. No. 8,763,245 to Lucisano et al. entitled "Hermetic feedthrough assembly for ceramic body," previously incorporated by reference herein). The working electrode 217 comprises an oxygen-detecting catalytic surface producing a glucose-modulated, oxygen-dependent current (discussed infra), reference electrode 218 comprises an electrochemical potential reference contact to electrolyte layer 250, and counter electrode 219 is operably connected by means of electrolyte layer 250 to the working electrode 217 and reference electrode 218. An electrical potentiostat circuit (not shown) is coupled to the electrodes 217, 218, and 219 to maintain a fixed potential between the working and reference electrode by passing current between the working and counter electrodes while preferably maintaining the reference electrode at high impedance. Such potentiostat circuitry is well known in the art (for an example, see U.S. Pat. No. 4,703,756 to Gough et al. entitled "Complete glucose monitoring system with an implantable, telemetered sensor module," incorporated herein by reference in its entirety).

The exemplary sensor apparatus of the present disclosure utilizes an "oxygen-sensing differential measurement," by comparison of the glucose-dependent oxygen signal (i.e., from the primary or enzyme-containing sensor elements) to the background oxygen signal (i.e., from the secondary non-enzyme-containing sensor elements) that produces, upon further signal processing, a continuous real-time blood glucose concentration measurement. It will be appreciated, however, that the methods an apparatus described herein are in no way limited to such "differential" schemes.

In one variant, the enzyme-embedded membrane includes embedded glucose oxidase (GOx) and catalase enzymes and the sensor elements are configured for detection of glucose based on the following two-step chemical reaction catalyzed by GOx and catalase as described in Armour et al. (*Diabetes* 39, 1519-1526 (1990)):

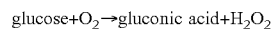
$$glucose + O_2 \rightarrow gluconic\ acid + H_2O_2$$

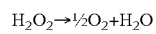
$$H_2O_2 \rightarrow \tfrac{1}{2}O_2 + H_2O$$

resulting in the overall enzyme reaction (when catalase is present):

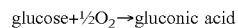
$$glucose + \tfrac{1}{2}O_2 \rightarrow gluconic\ acid$$

In one specific implementation, the two enzyme types (GOx and catalase, each in an excess concentration) are immobilized within a gel matrix that is crosslinked for mechanical and chemical stability, and is in operative contact with electrodes of each of the sensor elements, which are configured to electrochemically sense oxygen. Glucose and ambient oxygen diffuse into the gel matrix and encounter the enzymes, the above reactions occur, and oxygen that is not consumed in the process is detected by the electrodes. In embodiments based on "oxygen-sensing differential measurement" (i.e., comparison of an active sensor reading to a reference sensor reading), after comparison of the active oxygen concentration reading with the background oxygen concentration reading, the difference is related to glucose concentration. Thus, hydrogen peroxide produced in the initial GOx catalyzed reaction is digested to oxygen and water via the subsequent catalase catalyzed reaction, and glucose concentration may be determined via detection of oxygen. Accordingly, cell death and necrosis of the surrounding tissue due to hydrogen peroxide is mitigated, thereby at least partially mitigating the host wound healing response (as compared to hydrogen peroxide based detection sensors).

As can be seen in FIGS. 2 and 2A, the sensor pairs are radially arranged and substantially evenly spaced apart. An active sensor and a reference sensor are adjacent pairs of sensor elements such that the arrangement will allow each active sensor in the pair to remain within the same relatively homogenous region of the otherwise heterogeneous tissue in which the device is implanted.

The electrolyte layer 250 comprises, in the illustrated embodiment, a layer of hydrophilic electrolyte material which is in direct contact with the working electrode(s) 217, reference electrode(s) 218 and counter electrode(s) 219. In various implementations, materials for constructing the hydrophilic electrolyte layer 250 include salt-containing gels comprising polyacrylamide, poly(ethylene oxide), polyhydroxyethylmethacrylate and its derivatives, and other hydrophilic polymers and copolymers, in both crosslinked and non-crosslinked form. Various other construction details of the exemplary electrolyte layer 250 are described in U.S. Patent Application Publication No. 2013/0197332 filed Jul. 26, 2012 entitled "Tissue Implantable Sensor With Hermetically Sealed Housing," incorporated by reference herein in its entirety.

In an exemplary embodiment, the enzymatic material 240 comprises a crosslinked gel of hydrophilic material including enzymes (e.g., glucose oxidase and catalase) immobilized within the gel matrix, including a buffer agent and small quantities of a chemical crosslinking agent. The hydrophilic material 240 is permeable to both a large molecule component (e.g. glucose) and a small molecule component (e.g. oxygen). In various embodiments, specific materials useful for preparing the enzymatic material 240, include, in addition to an enzyme component, polyacrylamide gels, glutaraldehyde-crosslinked collagen or albumin, polyhydroxy ethylmethacrylate and its derivatives, and other hydrophilic polymers and copolymers, in combination with the desired enzyme or enzymes. The enzymatic material 240 can similarly be constructed by crosslinking glucose oxidase or other enzymes with chemical crosslinking reagents, without incorporating additional polymers.

The enzymatic material 240 is in operative contact with the working electrode 217 through the inner membrane 220 and the electrolyte layer 250 to allow for the electrochemical detection of oxygen at the working electrode 217 modulated by the two-step chemical reaction catalyzed by glucose oxidase and catalase discussed above. To that end, as glucose and ambient oxygen diffuse into the enzymatic material 240 from the outer (non-enzymatic) membrane 277, they encounter the resident enzymes (glucose oxidase and catalase) and react therewith; the oxygen that is not consumed in the reaction(s) diffuses through the inner membrane 220 and is detected at the working electrode 217 to yield a glucose-dependent oxygen signal. Advantageously, as discussed in greater detail below, any transiently created peroxide is scavenged by the catalase, which further enhances the non-immunogenic properties of the sensor as a whole.

A hydrophobic material is utilized for inner membrane 220, which is shown in FIG. 3 as being disposed over the electrolyte layer 250. The hydrophobic material is impermeable to the larger or less soluble molecule component (e.g. glucose) but permeable to the smaller or more soluble molecule component (e.g. oxygen). In various embodiments, materials useful for preparing hydrophobic layers, including inner membrane 220, as well as membrane shell 230, include organosilicon polymers, such as polydimethylsiloxane (PDMS) and derivatives thereof, polymers of tetrafluoroethylene, ethylene tetrafluoroethylene, or fluorochloro analogs alone or as copolymers with ethylene or propylene, polyethylene, polypropylene, cellulose acetate, and other oxygen-permeable polymeric materials.

The inner membrane 220 can also be a continuous layer across the entire detector array surface, and thus be a single common layer utilized by all detectors in the detector array (assuming a multi-detector array is utilized). It is noted that the inner membrane 220, inter alia, protects the working electrode 217, reference electrode 218 and counter electrode 219 from drift in sensitivity due to contact with certain confounding phenomena (e.g. electrode "poisoning"), but the working electrode 217 will nonetheless be arranged sufficiently close to the enzymatic material to enable detection of oxygen levels therein.

The (hydrophobic) outer membrane shell 230 is disposed over at least a portion of the enzymatic material 240 (forming a cavity 271 within which the material 240 is contained), and is further configured to include an aperture within a "spout" region 270. It is contemplated that the inner membrane 220 and the membrane shell 230 can be coextensive and therefore be disposed as one continuous membrane layer in which outer membrane shell 230 and inner membrane 220 are of the same uniform thickness of membrane across the individual detector and array, although it will be appreciated that other thicknesses and configurations may be used as well, including configurations wherein the membrane shell 230 is separately provided and adhesively bonded to the inner membrane 220.

However, as shown in FIG. 3, inner membrane 220 and membrane shell 230 are disposed in a manner that creates discrete three-dimensional regions having different thicknesses on the detector substrate 214, which can be utilized to create tissue anti-migration elements used to achieve stability of location, prevention of device migration away from its original implant location, and prevention of local tissue slippage in the vicinity of the detector element 206. Alternatively, the hydrophobic component may be dispersed as small domains in a continuous phase of the hydrophilic material. Various other construction details of the hydrophobic component dispersed as small domains in a continuous phase of hydrophilic material are described in U.S. Pat. Nos. 4,484,987 and 4,890,620, each incorporated herein by reference in its entirety.

As shown in FIGS. 3-3A, the single spout region 270 of the (primary) detector element 206 forms a small opening or aperture 276 through the membrane shell 230 to constrain the available surface area of hydrophilic enzymatic material 340 exposed for diffusionally accepting the solute of interest (e.g. glucose) from solution. Alternatively, it is contemplated that on or more spout regions (and or apertures within a spout region) can exist per detector element.

The shape and dimension of spout region 270 aids in controlling the rate of entry of the solute of interest (e.g. glucose) into enzymatic material 240, and thus impacts the effective operational permeability ratio of the enzymatic material 240. Such permeability ratio can be expressed as the maximum detectable ratio of glucose to oxygen concentration of an enzymatic glucose sensor, where such a sensor is based on the detection of oxygen unconsumed by the enzyme reaction, and after taking into account the effects of external mass transfer conditions and the enzyme reaction stoichiometry. Detailed discussions of the relationship between membrane permeability ratio and the maximum detectable ratio of glucose to oxygen concentration of oxygen-detecting, enzymatic, membrane-based sensors are provided in "Model of a Two-Substrate Enzyme Electrode for Glucose," J. K. Leypoldt and D. A. Gough, *Analytical Chemistry*, 56, 2896 (1984) and "Diffusion and the Limiting Substrate in Two-Substrate Immobilized Enzyme Systems," J. K. Leypoldt and D. A. Gough, *Biotechnology and Bioengineering*, XXIV, 2705 (1982), incorporated herein by reference. The membranes of the exemplary detector element described herein are characterized by a permeability ratio of oxygen to glucose of about 200 to about 1 in units of (mg/dl glucose) per (mmHg oxygen). Note that while this measure of permeability ratio utilizes units of a glucose concentration to an oxygen concentration, it is nevertheless a measure of the ratio of oxygen to glucose permeability of the membrane.

The exemplary spout 270 is formed out of the hydrophobic material of the membrane shell 230 without bonded enzymes (e.g., silicone rubber) and advantageously includes a non-enzymatic outer layer or membrane 277 to, inter alia, prevent direct contact of the immobilized enzymes in the enzymatic material 240 with the surrounding tissue, thereby mitigating tissue response (e.g., FBR), encapsulation, and/or other deleterious factors. In the exemplary embodiment, the non-enzymatic membrane 277 is further constructed (i.e., with a substantially planar, crosslinked biocompatible matrix possessing pores substantially smaller than those required to accommodate blood vessel ingrowth, but large enough to accommodate diffusion of solutes of interest) so as to frustrate or mitigate blood vessel formation therein.

Herein lies a salient feature of the sensor element of the exemplary embodiment; i.e., the combination of (i) an enzyme-free biocompatible outer membrane 277, (ii) maintenance of the spout region substantially free of enzyme material during manufacture, (iii) use of a low-pore diameter, crosslinked structure for the membrane 277, and (iv) use of a biocompatible material (e.g., silicone rubber) for the outer membrane shell 230, dramatically reduce the level of tissue response of the host while the device is implanted, thereby allowing for both longer implantation (due to, inter alia, the reduced level of tissue response not interfering with sensor operation) and easier explants of the device, as compared to e.g., peroxide-based sensors without one or more of such features. In one exemplary embodiment, the outer (non-enzymatic) membrane 277 has an average pore diameter on the order of five (5) to ten (10) microns, with the individual pore diameters distributed normally (i.e., according to a substantially Gaussian distribution function). See, e.g., Xiaoyu Ma, et al—"A Biocompatible and Biodegradable Protein Hydrogel with Green and Red Autofluorescence: Preparation, Characterization and In Vivo Biodegradation Tracking and Modeling," *Scientific Reports* (Nature.com) published Jan. 27, 2016, incorporated herein by reference in its entirety, for discussion of exemplary albumin-based substances and pore-size related features and considerations.

In another embodiment, the outer membrane has a maximum pore diameter value of less than 5 microns (i.e., on the order of 3 microns), such that the population of individual pores are substantially all below or equal to such value. In yet another implementation, a median pore diameter (which may be different than the aforementioned mean) is used as a basis for characterization of the outer membrane 277.

The inner hydrophobic membrane 220 further provides additional insulation of the host tissue in the region of the detector 206 against any electrical potentials or currents which may be present within the sensor element, thereby further aiding in mitigating any undesired tissue response. Further, use of a solid polymer layer 220 (e.g., formed of PDMS) disposed between the inner enzyme embedded membrane and sensing elements (i.e., electrodes) further assists in preventing passage of current from the electrodes into the surrounding tissues, and limiting possible exacerbation of tissue encapsulation (e.g., FBR, fibrosis, etc.) due to electrical flux, which may be problematic for some other conventional implanted sensors. Furthermore, the housing may be hermetically sealed to prevent exposure of tissue to electrical currents and/or internal components of the sensor.

In one example, an outer membrane 277 of a crosslinked albumin may be utilized. Additionally, other biostable polymers suitable as coating membranes include biocompatible materials, such as e.g., hydrophilic polyurethanes, silicones, poly(hydroxyethylmethacrylate)s, polyesters, polyalkyl oxides (polyethylene oxide), polyvinyl alcohols, polyethylene glycols, and polyvinyl pyrrolidone. Other polymers may also be used provided they can be dissolved, cured, or otherwise fixed or polymerized on the sensor housing. These may include polyolefins, polyisobutylene and ethylene-alphaolefin copolymers; acrylic polymers (including methacrylates) and copolymers, vinyl halide polymers and copolymers, such as polyvinyl chloride; polyvinyl ethers, such as e.g., polyvinyl methyl ether; polyvinylidene halides, such as e.g., polyvinylidene fluoride and polyvinylidene chloride; polyacrylonitrile, polyvinyl ketones; polyvinyl aromatics, such as e.g., polystyrene; polyvinyl esters, such as e.g., polyvinyl acetate; copolymers of vinyl monomers with each other and olefins, such as e.g., ethylene-methyl methacrylate copolymers, acrylonitrile-styrene copolymers, ABS resins and ethylene-vinyl acetate copolymers; polyamides, such as e.g., Nylon 66 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitrate; cellulose propionate; cellulose ethers, such as e.g., carboxymethyl cellulose and hydroxyalkyl celluloses; and combinations thereof. Polyamides for the purpose of this application would also include polyamides of the form —NH—$(CH_2)_n$—CO— and NH—$(CH_2)_x$—NH—CO—$(CH_2)_y$—CO, wherein n is preferably an integer in from 6 to 13, x is an integer in the range of form 6 to 12, and y is an integer in the range of from 4 to 16.

It will be appreciated that the relatively smaller dimensions of the sensor apparatus (as compared to many conventional implant dimensions)—on the order of 40 mm in length (dimension "a" on FIGS. 2A-2C) by 25 mm in width (dimension "b" on FIGS. 2A-2C) by 10 mm in height (dimension "c" on FIGS. 2A-2C)—may reduce the extent of injury (e.g., reduced size of incision, reduced tissue disturbance/removal, etc.) and/or the surface area available for blood/tissue and sensor material interaction, which may in turn reduce intensity and duration of the host wound healing response. It is also envisaged that as circuit integration is increased, and component sizes (e.g., lithium or other batteries) decrease, and further improvements are made, the sensor may increasingly be appreciably miniaturized, thereby further leveraging this factor.

It is also appreciated that some flexibility in component location exists; as such, the present disclosure further contemplates e.g., relocation of certain components within the implanted sensor device 200 such as those associated with signal processing, off-device (i.e., in an external receiver module or other electronic apparatus external to the implanted sensor, such as a user's smartphone or tablet computer, or other implanted or external medical device) so as to further minimize interior sensor device volume/area requirements. For instance, in one such adaptation, electronic components such as antennas and/or circuit boards (e.g., PCBs) can be wholly or partly replaced with so-called "printable" electronics which reside on, e.g., interior components or surfaces of the sensor device 200, such as by using the methods and apparatus described in U.S. Pat. No. 9,325,060 issued Apr. 26, 2016 and entitled "Methods and apparatus for conductive element deposition and formation," which is incorporated herein by reference in its entirety. Other types of space/area-reducing adaptations will be readily recognized by those of ordinary skill in the electronic arts when given the present disclosure.

Returning again to FIGS. 2-2C, the housing 202 and sensing region 204 purposely have relatively smooth outer surfaces, which may be comprised of biocompatible materials, thereby limiting reaction of the tissue to the sensor apparatus 200 and allowing long-term implantation. Specifically, by providing a smooth surface over much of the sensor housing and forming the housing (and other externally exposed components) of materials which do not incite tissue response (e.g., titanium), very little if any bonding or attachment of the tissue response to the sensor housing or other such components occurs, even after an extended period of implantation (i.e., 12 months or more). Biocompatible materials may be used at least where any portion of the sensor comes into physical contact with the body. Exemplary biocompatible materials are disclosed in U.S. Patent Publication No. 20130197332, previously incorporated herein. A variety of suitable medical grade materials are known in the art which may be utilized to construct the housing; e.g., a metallic material or an alloy such as, but not limited to, bio-inert metals, cobalt-chromium alloys, alloys of cobalt, nickel, chromium and molybdenum, stainless steel, tantalum, tantalum-based alloys, nickel-titanium alloy, platinum, platinum-based alloys such as e.g., platinum-iridium alloy, iridium, gold, magnesium, titanium, titanium-based alloys, zirconium-based alloys, or combinations thereof. Further, the housing may be constructed from biocompatible ceramic materials, comprising oxides, carbides, borides, nitrides, and silicides of aluminum, zirconium, beryllium, silicon, titanium, yttrium, hafnium, magnesium and zinc.

Furthermore, the housing may also be made from biocompatible, biostable polymers, such as polymers including but not limited to fluorpolymers (e.g., DuPont Teflon® or Tefzel® or the like), epoxy resins, polyetherimides, poly ether ketone, polysulfone, polyphenylsulfone, polypropylene, polycarbonate, poly methyl methacrylate, and others, which may present a smooth and substantially non-adherent surface in certain formulations.

Figure 5:
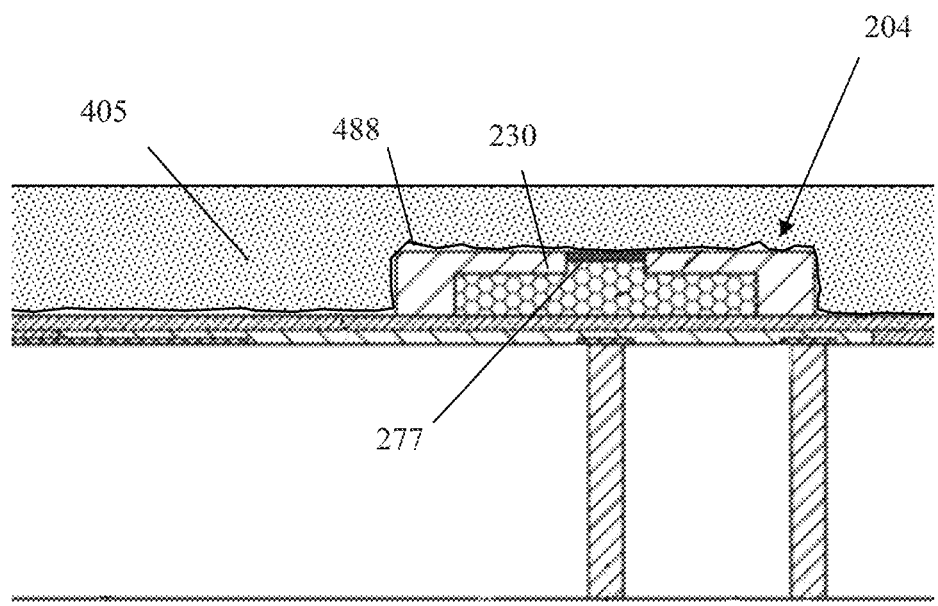
FIG. 5 is a side cross-sectional detail view of a detector element of the sensor apparatus of FIGS. 2-3A, illustrating the "interlocking" of tissue/tissue response therewith after implantation as in FIG. 4.

Notably, however, the sensing region 204 of the exemplary sensor apparatus 200 purposely includes some level of texture or relief (albeit with biocompatible materials as well), so as to give any tissue response or encapsulation in that region something to "grab onto" to promote the close contact, interlock, and anti-slip described herein with respect to FIG. 5. Such texture or relief can be provided in one or more ways, including e.g., via a roughened or "bumpy" material texture, and/or one or more prominent or salient features elevated and/or depressed over/within the surrounding portions of the apparatus (i.e., irrespective of texture of the materials). As previously referenced, this arrangement also helps maintain the sensor element active areas (i.e., the outer non-enzymatic membrane 277 and its underlying enzyme in the "primary" sensor elements, and the membrane 277 with non-enzymatic matrix in the "secondary" sensor elements) maintain a substantially constant, direct, and non-variable level of contact with particular blood vessels located in the tissue of that region, so as to maximize the stability and accuracy of the signals generated from each of the sensor elements. Specifically, the absence of relative motion between each individual sensor primary or secondary element and the surrounding tissue and vasculature allows the sensor to receive a substantially constant blood (and hence glucose) supply over time, which translates to a substantially constant rate of glucose diffusion through the outer membrane 277 and into the underlying matrix.

Implantation to Minimize Tissue Response and Maximize Detector Contact

Previously incorporated U.S. patent application Ser. No. 14/982,346 filed Dec. 29, 2015 and entitled "Implantable Sensor Apparatus and Methods" describes exemplary "deep" implantation techniques useful with the apparatus and methods of the present disclosure; specifically, in the exemplary embodiment of such techniques, the sensor apparatus 200 is implanted surgically near the abdominal muscle fascia and in contact with the solid tissue within a pocket formed in the host's lower abdomen; see FIG. 4 herein. Specifically, once the cavity or pocket 401 is formed, the sensor apparatus 200 is implanted within the cavity/pocket in the direction 400 shown, so that the sensing region 204 is both proximate the target fascial layer (and contacting the local solid tissue) and oriented in the desired direction. In one variant, the user's superficial (scarpal) fascia is incised, and the adipose tissue 405 immediately proximate the deeper fascial membrane 402 (i.e., anterior abdominal fascia; see FIG. 4) is merely separated from the fascial membrane so as to form the desired cavity or pocket 401, with little or no tissue removal from the patient. Such separation is preferably performed using "blunt" techniques (i.e., without cutting per se), to minimize tissue and blood vessel trauma, and also mitigate prospective FBR (which may be exacerbated from cutting versus blunt formation), but may also be performed using an instrument such as a scalpel or surgical scissors if needed or desired for other reasons.

As described supra, in addition to potentially creating inconsistencies or variations in interaction between each sensor element and its surrounding vasculature (and hence reducing inter alia, device accuracy over time), undesired movement of the implanted sensor apparatus may also contribute to increased chronic inflammation (which can have its own set of deleterious effects). Therefore, limiting undesired movement may also advantageously mitigate the host's tissue response to the implanted sensor. The somewhat planar shape of the sensor housing 202 helps to maintain the desired sensor orientation and placement; accordingly, the sensor apparatus 200 is inserted into the cavity 401 with the "flat" sides substantially parallel to the plane of the fascial layer 402, musculature 404, superficial fascia 406, superficial fatty tissue layer 407, and epidermis 408. In one variant, the sensor apparatus 200 is oriented "round side up", such that the rounded end 211 (see FIG. 2) is inserted into the formed pocket first, thereby aiding in placement with minimal friction and effort.

The mechanical stability provided by the substantially planar shape of the housing 202 after implantation helps to preserve the orientation of the apparatus 200 (e.g., with sensing region 204 facing away from the epidermis and toward the proximate fascial layer), resisting rotation around its longitudinal axis 208, and translation, or rotation about its transverse axis 210, which might otherwise be caused by e.g., normal patient ambulation or motion, sudden accelerations or decelerations (due to e.g., automobile accidents, operation of high-performance vehicles such as aircraft), or other events or conditions.

Notwithstanding, the present disclosure contemplates sensor apparatus of shapes and/or sizes other than that of the exemplary apparatus 200, including use of means for maintaining the desired orientation and position such as e.g., the plurality of tabs or anchor apparatus 213 disposed substantially peripheral on the apparatus housing (FIGS. 2A-2C), which provide the implanting surgeon with the opportunity to anchor the apparatus to the anatomy of the living subject, so as to further frustrate translation and/or rotation of the sensor apparatus 200 within the subject immediately after implantation but before any tissue response of the host has a chance to immobilize the device, such as via interlock with the sensing region of the apparatus discussed below with respect to FIG. 5).

The sensor apparatus may additionally or alternatively include one or more anti-migration features described in U.S. Pat. No. 7,871,456, and U.S. Patent Publication No. 20130197332, each of which is previously incorporated herein. In one variant, an outer surface of the housing may include one or more anti-migration elements, which promote adherence of the sensor apparatus to the surrounding tissue. In some embodiments, a biocompatible mesh, fabric or three-dimensional structure comprised of e.g., polymeric, metallic, and/or ceramic materials may be disposed on a surface of the housing for encouraging ingrowth of tissues (e.g., via tissue regeneration and/or fibrosis) into such anchor or anti-migration elements. In other embodiments, tissue anti-migration elements may also include coatings or agents for enhancing or promoting cellular attachment as well as ingrowth, such as cell adhesion molecules, e.g., fibronectin and laminin, as well as anti-thrombotic and/or anti-platelet agents, such as e.g., heparin.

As noted above, undesired movement (translation, rotation) of the sensor apparatus is further inhibited after implantation through physiological interaction (e.g., tissue regeneration, FBR, fibrosis, etc.) of the sensor apparatus with the host subject at the site of implantation. For example, clinical trials of the exemplary apparatus 200 by the Assignee hereof indicate that some degree of tissue "contouring" or "imprinting" with at least the sensing region 204 (e.g., a raised sensing region) occurs over the duration of a typical implantation, due to inter alia normal biological processes within the host, as shown in the depiction of FIG. 5. In effect, the host's tissue 405 closely contacts and develops contours directly reflective of the shape of the sensing region 204 (and specifically the outer membrane element 230 and non-enzymatic membrane 277), thereby indirectly providing enhanced mechanical coupling, and attendant resistance to movement. Vascularization (i.e., the in-growth of micro-sized blood vessels) into the sensor element outer membrane 230 and non-enzymatic membrane 277 is also advantageously and purposely frustrated as previously noted, thereby making the implanted sensor apparatus readily separated from the surrounding solid tissue 405 at explant, even after extended periods of time, since few if any such blood vessels need be severed to effect physical separation of the device from the tissue in the sensing region 204, as well as other portions of the device housing as previously described. Hence, the exemplary apparatus and techniques of the present disclosure cooperate to enable a small but deep implantation of the device 200 which advantageously immobilizes it, maintains constant and predictable blood vessel and sensor contact, yet engenders very little tissue response and encapsulation, and little if any vascularization, thereby both mitigating effects of such confounding tissue response on the detector elements 206, and making for easy subsequent explants.

It is appreciated that some degree of separation or "gaps" 488 may exist between the host tissue and the sensor element outer components (as shown in FIG. 5) due to e.g., recesses or artifacts present in the shape of the outer sensor components, or for biological reasons; however, so long as substantially intimate contact is maintained over a majority of the surface areas of the detector sensing region 204, the correlation of the detector output with analyte concentration within the blood vessels of the neighboring tissue remains stable, helping to ensure sensor overall sensor accuracy and utility.

As described supra, it is also envisaged that as circuit integration is increased, and component sizes (e.g., lithium or other batteries) decrease, and further improvements are made, the sensor may increasingly be appreciably miniaturized, and further that successively smaller and smaller incisions are required for implantation of the sensor apparatus over time. Laparoscopic implantation, or even a coarse "injection" delivery by trocar are also feasible methods of implantation with appropriate adaptation, such adaptation being well within the skill of an ordinary artisan in the medical or surgical arts when given the present disclosure. It will be appreciated that the smaller dimensions of the sensor apparatus may reduce the extent of injury (e.g., eliminate need for an incision during implantation, reduced size of incision, reduced tissue removal, etc.), which in turn may reduce intensity and/or duration of the host wound healing response, thereby even further leveraging the advantageous aspects of the methods and apparatus disclosed above.

In one variant, the detectors of the sensor apparatus 200 are also advantageously insensitive to interfering or confounding substances; e.g., low molecular weight species such as acetaminophen (e.g., Tylenol®—$C_8H_9NO_2$; molecular weight 151.16). As is known, while the glucose oxidase enzyme is highly specific to the glucose molecule, migration of acetaminophen through to the sensing electrodes can adversely impact operation of a peroxide-based implantable glucose sensor, such adverse impact being severe enough to warrant contra-indication of acetaminophen for the host during monitoring. Contra-indication of such a common pain reliever is highly undesirable from a practical standpoint; the host must strictly utilize an alternate over-the-counter pain reliever which is not contra-indicated. Moreover, one errant ingestion by the host during monitoring (e.g., mistakenly swallowing acetaminophen versus a non-contra-indicated substance) can cause significant errors in the estimated blood glucose level, often in a non-conservative direction which can even be life-threatening to the host (i.e., erroneously indicating that the subject has a greater blood glucose level than they actually do, and either causing the host to treat the erroneously-elevated glucose level with glucose-lowering medication or avoid taking action which could otherwise mitigate an actual low blood glucose condition).

Such issues are avoided by the exemplary sensor configuration through, inter alia, use of an oxygen-based electrode apparatus which is effectively insensitive to oxidizing agents such as acetaminophen. Specifically, the exemplary sensor apparatus 200 couples the highly-specific enzyme glucose oxidase to electrodes sensitive to oxygen, eliminating the influence from non-glucose substances. Utilizing an oxygen-sensitive electrode also allows the co-localization of catalase, a high affinity enzyme that converts the hydrogen peroxide produced by the glucose oxidase to water and oxygen. This prevents release of the hydrogen peroxide into the surrounding tissues, minimizing inflammation and the foreign body response, while having an additive benefit of regenerating half of the oxygen consumed by glucose oxidase. Notwithstanding, the inner membrane of the sensor apparatus 200 may be configured to block or interfere with the permeation of undesirable species such as acetaminophen. In one variant, such blockage of undesired species is accomplished through use of an inner membrane having a prescribed pore size; i.e., large enough to permit the migration of oxygen molecules to the electrodes, yet small enough to block undesired species such as acetaminophen. See, e.g., U.S. Pat. No. 5,804,048 entitled "Electrode assembly of assaying glucose", incorporated herein by reference in its entirety, which describes one exemplary approach to utilizing a membrane within a glucose sensor to block undesirable molecular species from reaching sensing electrodes, although it is appreciated that other approaches may readily be used consistent with the present disclosure.

Anecdotal Performance

Human clinical trials conducted by the Assignee hereof authorized by the U.S. Food and Drug Administration (FDA) to date indicate superior performance of the foregoing techniques and apparatus, including notably (i) the ability of the sensor apparatus to remain implanted for extended periods without deleterious foreign body response to the sensor from the host which impairs the operation of the sensor, (ii) general insensitivity to ingested or locally injected substances which might otherwise interfere with the performance of the device (e.g., acetaminophen, insulin injections, etc.) and (iii) the ability of the sensor apparatus to provide a stable output for extended (e.g., multiple week) intervals. These advantages are due at least in part by virtue of the selected target location being deep(er) within the abdominal subcutaneous tissue of the patient (e.g., proximate the fascia), and the orientation of the sensing region of the apparatus 200 away from possible sources of interference or degradation, as well as construction details described above (e.g., use of a non-enzymatic outer membrane, maintenance of the aperture of the sensor outer membrane or housing enzyme-free, insulation of electrical currents or potentials, use of biocompatible materials, use of sensing region shape and construction which promotes close contact and interlock with the surrounding tissue, and minimization of the size of the implanted device).

Figure 6:
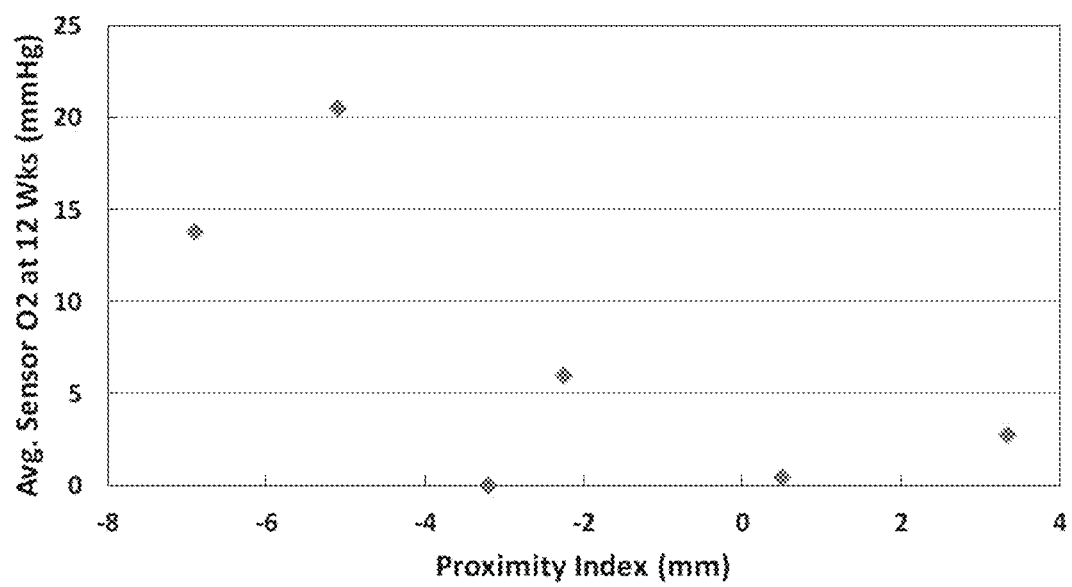
FIG. 6 herein is a plot of "proximity index" vs. average sensor $O_2$ level at 12 weeks (implanted duration) obtained during clinical trials by the Assignee hereof using an exemplary sensor device similar to that of FIG. 2.

FIG. 6 herein is a plot of "proximity index" vs. average sensor $O_2$ level at 12 weeks (implanted duration), which illustrates exemplary anecdotal data obtained by the Assignee hereof during trials of a generally comparable sensing device and using, inter alia, ultrasound techniques. Specifically, the data of FIG. 6 demonstrates the aforementioned stability of output for extended periods, which is in part afforded by the sensor device's access to the blood supply by virtue of its "deep" placement and mitigation of tissue response as noted above.

Each point on the graph of FIG. 6 represents the average of the output from the four (4) oxygen reference or "secondary" electrodes on a given implanted device. The "proximity index" metric of FIG. 6 provides an indication of the distance between the sensing area aspect of the implanted device and the underlying muscle layer. Any positive value of the index indicates physical separation (i.e., lack of intimate contact between the sensing area and the target tissue such as the muscle fascia). Conversely, any negative index value indicates close contact between the sensing area and the muscle fascia. Hence, as can be seen in FIG. 6, where close physical contact of the sensing area of the device and the muscle fascia was maintained, including the aforementioned "interlock" of the tissue with the sensing area, sensor output was notably elevated compared to cases where close contact between the sensing area of the device and the muscle fascia was not achieved.

Imprint Re-Use Methods

Figure 7:
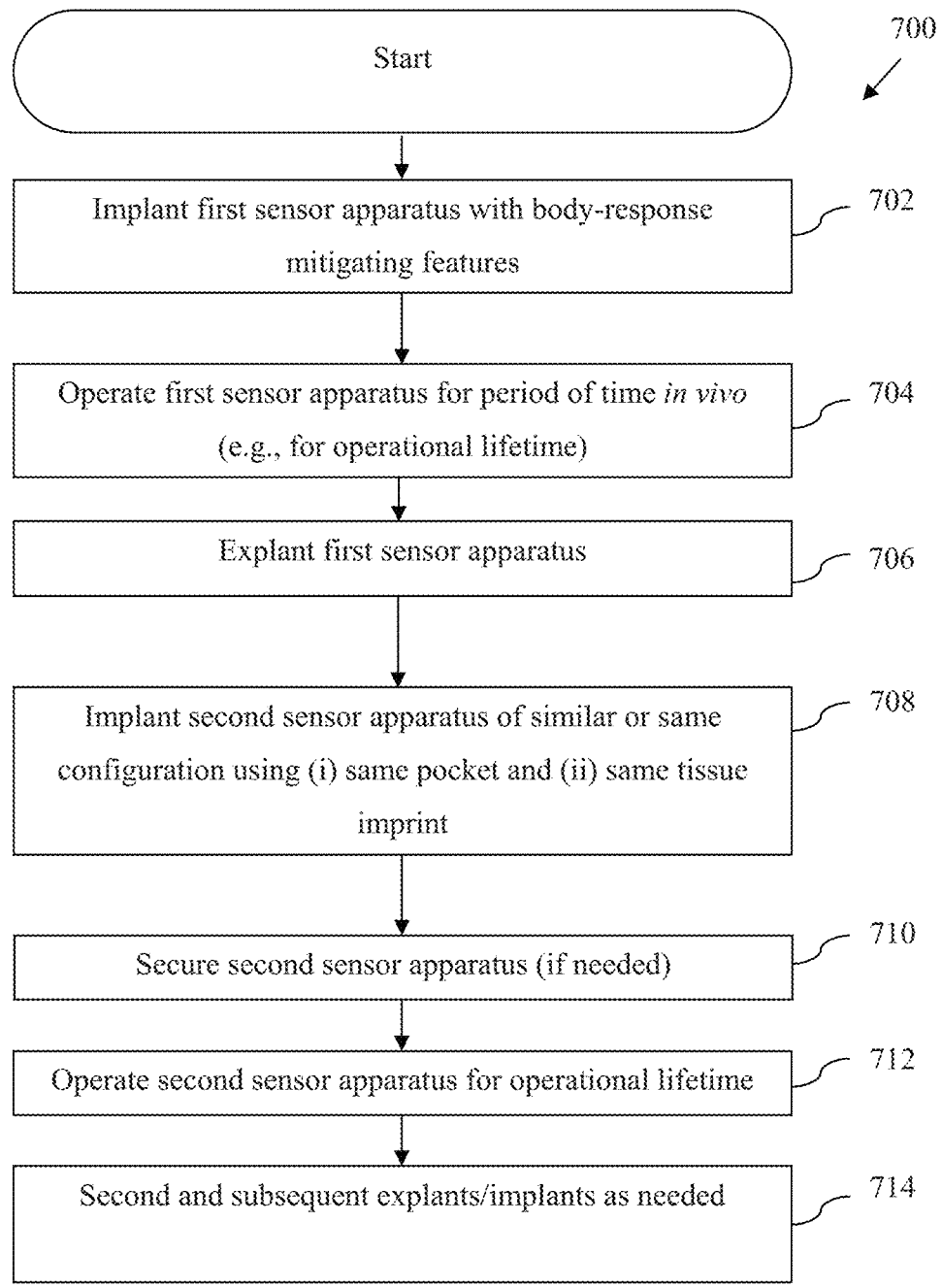
FIG. 7 is a generalized logical flow diagram illustrating an exemplary embodiment of a method of surgical implantation leveraging tissue "imprint" according to the present disclosure.

Referring now to FIG. 7, methods of surgical implantation leveraging the tissue "imprint" previously described herein are discussed in detail. Specifically, as noted supra, the foregoing imprint created by the sensor apparatus 200 upon continued implantation within a host for a period of time can be advantageously re-used, whether by (i) a subsequent replacement sensor of the same or similar configuration as that originally implanted, or (i) the same sensor apparatus that has been e.g., explanted, refitted with a new battery or other component(s), or otherwise made suitable for re-implantation, so that the foreign body response or other deleterious host responses are yet further avoided, and trauma to the host is minimized. As noted, the construction of the exemplary sensor apparatus 200 includes biocompatible materials and other features (including albumin outer membrane in some implementations) which enable the surrounding host tissue to come in close physical contact with the sensor apparatus (and especially the sensing region thereof), yet avoid any significant bonding or attachment thereto. Hence, explant of the sensor apparatus (even after significant periods of time, such as 12 months or more) is readily conducted, with effectively no trauma to the contacting tissue (i.e., the sensor apparatus more or less "peels away" from the tissue without significant damage or alteration thereto, since there is effectively no bonding or blood vessel vascularization into or onto the sensor apparatus).

Hence, after explant, the imprint on the tissue remains essentially intact, and can be utilized by the subsequently implanted sensor apparatus (assuming similar configuration in at least the sensing region). This approach yet further mitigates body response that might occur from the explant and subsequent implant. Moreover, when using the "deep" surgical implantation techniques previously described and incorporated by reference herein, and a substantially identical replacement sensor configuration, the same surgical incision, pocket, and sensor orientation can be utilized—the host in effect sees the replacement apparatus as an exact fit for the explanted device (same size, same materials, etc.), and hence no further body response is generated. This process of explant and replacement with a similar apparatus in the same pocket and imprint can be performed almost indefinitely, since (i) the duration of implantation is long (e.g., 12 months or more) and hence the (reused) incision has plenty of time to heal; and (ii) the lack of any subsequent significant body response avoids any other processes within the body which might otherwise limit reuse of the same implantation location on the host.

Moreover, by using the same imprint within the tissue, the replacement sensor apparatus is immediately "locked into" position (contrast the original implantation, wherein a period of time is required for the host tissue to imprint or form closely around all of the features of the sensor apparatus as in FIG. 5), and hence any body response due to e.g., relative movement between the sensor apparatus 200 and surrounding tissue, is substantially avoided. It is envisioned that in certain cases, such immediate position lock on the second and subsequent implants can even be used as a basis for selectively obviating use of dissolvable sutures or other anchoring mechanisms described herein, since the imprint (and other contours developed around the prior sensor apparatus in the pocket) effectively perform the same function. Obviating trauma (however mild) due to e.g., suturing may yet further mitigate formation of any undesired body response.

As shown in FIG. 7, the exemplary embodiment of the method 700 first includes implantation of the "first" sensor apparatus (original, or otherwise) into the host using, e.g., the implantation techniques previously described, per step 702.

Next, the implanted sensor apparatus is operated in vivo; e.g., until it has reached its design implantation duration, its battery is showing signs of expiration, (e.g., via voltage readings across its terminals, etc.), or based on yet other criteria, ideally using the same incision as used for implantation (step 704).

The implanted sensor is then explanted (step 706), and a "second" sensor apparatus (which may be the same as originally implanted, or another of similar design/configuration as described above) is implanted, and oriented as identically as possible to the orientation of the first sensor apparatus (step 708). During implantation, the implanted (second) apparatus is secured if/as needed, such as via dissolvable suture (step 710). The second sensor is then operated for its prescribed period (e.g., operational lifetime) per step 712, and then subsequently explanted and replaced as needed per step 714, i.e., similar to steps 706 through 712.

Adaptation Circuitry and Methods

In some cases of implantation, the FBR and/or fibrosis phases of wound healing may block or cover one or more of the sensor elements 206. The sensor apparatus, however, includes multiple (4) sets of sensing and reference sensing elements, which are in one implementation adapted to dynamically compensate for e.g., FBR, fibrosis, or other so-called "confounding factors" (described in U.S. Pat. No. 7,248,912, previously incorporated herein) occurring proximate the sensing elements, thereby maintaining the accuracy of the device as a whole. Specifically, the sensor apparatus 200 may have the advantage that the active sensor reading is compared to the reference sensor for glucose detection (i.e., "oxygen-sensing differential measurement", described supra). Thus, if the active sensor is blocked by foreign body giant cells, granulation tissues, and/or fibrous host tissue, it is likely that the adjacent reference sensor is also blocked. Readings from the sensing element pair will indicate that they are non-functional and should be excluded from determining the diabetic patient's glucose level.

The sensor apparatus 200 has the further advantage that if one or more pairs of sensors are non-functional, the glucose level may be determined from the remaining sensor pairs. Accordingly, as sensing elements or sets thereof become inoperative or unreliable, these elements/sets can be selectively removed from the signal processing logic and deactivated while other sensor pairs remain active. Alternatively, the weight of any signals generated by such compromised elements or pairs may be reduced over time so as to progressively reduce their contribution to the "composite" signal generated by the device.

Moreover, the aforementioned ability to remove or reduce the contribution of a given detector element or pair enables compensation for detector failure due to, e.g., leakage or other fault. As noted elsewhere herein, the exemplary sensor apparatus maintains the regions of each detector contacting the host's solid tissue enzyme-free (both through use of the non-enzymatic membrane 277 of FIG. 3 and manufacturing processes which avoid contamination of the spout region 370 with the enzyme matrix of the cavity), and electrically insulated. However, in the case of a manufacturing defect, failure of a component (e.g., non-enzyme membrane 277 or outer membrane 230), or other such occurrence, the tissue response in a region localized to that (failed) detector element may increase due to the presence of the enzyme, electrical stimulation, etc., which can result in degradation of the performance of that particular detector element (if not already degraded due to component failure). By identifying such failures or tissue responses, the affected detector(s) can be electrically removed from further signal processing while the sensor 200 is implanted.

Exemplary apparatus and methods for evaluating and adjusting operation of an implanted analyte (e.g., glucose) sensor which may be used consistent with the present disclosure are described in U.S. Pat. No. 7,248,912 to Gough, et al. issued Jul. 24, 2007 and entitled "Tissue implantable sensors for measurement of blood solutes", previously incorporated herein, although it will be appreciated that other apparatus and methods may be used alternatively or in addition to those described in U.S. Pat. No. 7,248,912.

It will be recognized that while certain embodiments of the present disclosure are described in terms of a specific sequence of steps of a method, these descriptions are only illustrative of the broader methods described herein, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure and claimed herein.

While the above detailed description has shown, described, and pointed out novel features as applied to various embodiments, it will be understood that various omissions, substitutions, and changes in the form and details of the device or process illustrated may be made by those skilled in the art without departing from principles described herein. The foregoing description is of the best mode presently contemplated. This description is in no way meant to be limiting, but rather should be taken as illustrative of the general principles described herein. The scope of the disclosure should be determined with reference to the claims.

What is claimed is:

1. An analyte sensor, comprising:
    a biocompatible housing having a size and a shape suitable for implantation in a body;
    a plurality of glucose-modulated oxygen detectors, at least a working electrode of each of the plurality of glucose-modulated oxygen detectors in communication with at least one glucose oxidase and catalase-embedded material, the at least one glucose oxidase and catalase-embedded material enclosed in a membrane structure, the membrane structure configured to provide a barrier between biological tissues of the body and the at least one glucose oxidase and catalase-embedded material at least when the analyte sensor is implanted in a tissue environment within the body;
    circuitry operatively connected to the plurality of glucose-modulated oxygen detectors and configured to process at least a portion of signals generated by at least a portion of said plurality of glucose-modulated oxygen detectors to produce processed signals;
    one or more wireless data transmission apparatus configured to transmit at least a portion of said processed signals; and
    an electrical power source operatively coupled to at least the circuitry and the data transmission apparatus and configured to provide electrical power thereto;
    wherein said circuitry at least in part comprises processing logic which is configured to:
    identify one or more of the plurality of glucose-modulated oxygen detectors which each experience signal variations caused by biological processes within the body after the analyte sensor has been implanted in the tissue environment within the body;

based at least in part on the identification, selectively remove glucose-modulated signals respectively generated by the identified one or more of the plurality of glucose-modulated oxygen detectors from processing of a composite glucose-modulated signal; and generate the composite glucose-modulated signal from other glucose-modulated signals respectively generated by one or more remaining non-identified ones of the plurality of glucose-modulated oxygen detectors which have not experienced the signal variations, the composite glucose-modulated signal useful for calculation of a blood glucose level value.

2. The analyte sensor of claim 1, wherein:

the signal variations caused by biological processes within the body are caused by tissue response of the body due to implantation of the analyte sensor; and the selective removal of the glucose-modulated signals respectively generated by the identified one or more of the plurality of glucose-modulated oxygen detectors from processing of the composite glucose-modulated signal comprises substitution of first glucose-modulated signals generated by the one or more remaining ones of said plurality of glucose-modulated oxygen detectors of said analyte sensor that have not experienced said signal variations for second glucose-modulated signals generated by the one or more of said plurality of glucose-modulated oxygen detectors that have experienced said signal variations.

3. The analyte sensor of claim 1, wherein the processing logic is further configured to, based at least on the identification of the one or more of the plurality of glucose-modulated oxygen detectors which each experience signal variations, implement an automatic signal scaling process.

4. The analyte sensor of claim 1, wherein the selective removal of the glucose-modulated signals respectively generated by the identified one or more of the plurality of glucose-modulated oxygen detectors from the processing of a composite glucose-modulated signal at least in part comprises:

selective decrease of a weight value associated with the glucose-modulated signals respectively generated by the identified one or more of the plurality of glucose-modulated oxygen detectors during the processing by the circuitry and generation of the composite glucose-modulated signal; and selective increase of a weight value associated with the other glucose-modulated signals respectively generated by the one or more remaining non-identified ones of the plurality of glucose-modulated oxygen detectors which have not experienced the signal variations during the processing by the circuitry and generation of the composite glucose-modulated signal.

5. The analyte sensor of claim 4, the selective decrease of the weight value-associated with the glucose-modulated signals respectively generated by the identified one or more of the plurality of glucose-modulated oxygen detectors and the selective increase of the weight value associated with the other glucose-modulated signals respectively generated by the one or more remaining non-identified ones of the plurality of glucose-modulated oxygen detectors which have not experienced the signal variations enable the fully subcutaneous implantation and operation of the analyte sensor for at least one year without explant thereof.

6. The analyte sensor of claim 4, wherein the selective decrease of the weight value associated with the glucose-modulated signals respectively generated by the identified one or more of the plurality of glucose-modulated oxygen detectors comprises incremental decrease of the weight value associated with the glucose-modulated signals respectively generated by the identified one or more of the plurality of glucose-modulated oxygen detectors over a period of time of operation of the analyte sensor.

7. The analyte sensor of claim 1, wherein the membrane structure for each of the plurality of glucose-modulated oxygen detectors at least in part comprises a porous cross-linked protein-based material having a plurality of pores of a prescribed pore diameter at least on an outer surface of the membrane structure, the prescribed pore diameter configured to, when the analyte sensor is disposed in the tissue environment within the body, both (i) frustrate vascularization therein, and (ii) permit migration of blood glucose therethrough.

8. The analyte sensor of claim 7, wherein the plurality of pores of the prescribed pore diameter comprises one of: (i) a plurality of pores of an average pore diameter of approximately 5 microns, or (ii) a plurality of pores of a median pore diameter of approximately 5 microns.

9. The analyte sensor of claim 7, wherein the plurality of pores of the prescribed pore diameter comprises a plurality of pores of an average pore diameter in the range of 5 to 10 microns inclusive.

10. The analyte sensor of claim 7, wherein the plurality of pores of the prescribed pore diameter comprises a plurality of pores having a maximum of 5 microns for each of the plurality of pores.

11. The analyte sensor of claim 7, wherein the porous crosslinked protein-based material is formed from a flowable protein-based material which is subsequently exposed to a cross-linking agent to form a non-flowable protein-based material having the plurality of pores of the prescribed pore diameter.

12. The analyte sensor of claim 1, wherein the membrane structure comprises a plurality of respective membranes each configured to insulate the biological tissues from respective ones of the at least one glucose oxidase and catalase-embedded material of each of the plurality of glucose-modulated oxygen detectors at least when the analyte sensor is disposed in the tissue environment within the body.

13. The analyte sensor of claim 12, wherein each of the plurality of respective membranes comprises a mostly enzyme-free chemically crosslinked albumin-based material.

14. The analyte sensor of claim 1, wherein the at least one glucose oxidase and catalase-embedded material is configured to at least transiently produce hydrogen peroxide in a reaction with blood glucose.

15. The analyte sensor of claim 1, wherein the membrane structure comprises, for each of the plurality of glucose-modulated oxygen detectors:

an outer body element having at least one aperture formed therein, the outer body element defining an interior cavity, wherein the at least one glucose oxidase and catalase-embedded material is disposed within the interior cavity; and a non-enzymatic membrane material disposed at least partly within the at least one aperture.

16. The analyte sensor of claim 15, wherein:

at least the outer body element is configured to electrically insulate the biological tissues from the working electrode during operation when the analyte sensor is disposed in the tissue environment within the body.

17. The analyte sensor of claim 16, wherein:
the outer body element configured to electrically insulate the biological tissues from the working electrode during operation comprises an electrically insulating membrane configured to be disposed between at least the working electrode and the biological tissues when the analyte sensor is disposed in the tissue environment within the body; and wherein the electrically insulating membrane disposed between at least the working electrode and the biological tissues comprises silicone rubber.

18. The analyte sensor of claim 1, wherein said circuitry at least in part comprises processing logic which is further configured to:
based at least in part on the identification, deactivate the identified one or more of the plurality of glucose-modulated oxygen detectors.

19. The analyte sensor of claim 1, wherein the signal variations caused by biological processes comprises signal variations over time due to one or more foreign body response (FBR) processes.

20. The analyte sensor of claim 1, wherein the signal variations caused by biological processes comprises signal variations over time due to one or more of (i) variations in vascularization, or (ii) long-term variations in blood flow.

21. The analyte sensor of claim 1, wherein the identification of the one or more of the plurality of glucose-modulated oxygen detectors comprises a determination that at least one of an active sensor and a reference sensor of the identified one or more of the plurality of glucose-modulated oxygen detectors fails to meet one or more criteria related to signal stability.

22. The analyte sensor of claim 1, wherein said circuitry at least in part comprises processing logic which is configured to:
based at least in part on the identification, deactivate an active sensor and a reference sensor of the identified one or more of the plurality of glucose-modulated oxygen detectors.

23. An analyte sensor, comprising:
a biocompatible housing having a size and a shape suitable for implantation in a body;
a plurality of glucose-modulated oxygen detectors each comprising an enzymatic material, the enzymatic material enclosed in a membrane structure, the membrane structure configured to provide a barrier between biological tissues of the body and the enzymatic material at least when the analyte sensor is implanted in a tissue environment within the body;
circuitry operatively connected to the plurality of glucose-modulated oxygen detectors and configured to process at least a portion of signals generated by at least a portion of said plurality of glucose-modulated oxygen detectors to produce processed signals;
wireless data transmission apparatus configured to transmit data relating to said processed signals; and
an electrical power source operatively coupled to at least the circuitry and the data transmission apparatus and configured to provide electrical power thereto;
wherein said circuitry at least in part comprises processing logic which is configured to:
identify at least one of the plurality of glucose-modulated oxygen detectors which experiences unacceptable signal performance after the analyte sensor has been implanted in the tissue environment within the body;
based at least in part on the identification, selectively remove glucose-modulated signals generated by the identified at least one of the plurality of glucose-modulated oxygen detectors from generation of a composite glucose-modulated signal, the composite glucose-modulated signal generated using only one or more remaining non-identified ones of the plurality of glucose-modulated oxygen detectors, the composite glucose-modulated signal useful for calculation of a blood glucose level value.

24. The analyte sensor of claim 23, wherein the processing logic is further configured to utilize the composite glucose-modulated signal to calculate at least one blood glucose level value.

25. The analyte sensor of claim 24, wherein the analyte sensor is configured to utilize the wireless data transmission apparatus to wirelessly transmit the at least one blood glucose level value to a data receiver device disposed external to the body.

26. The analyte sensor of claim 24, wherein the analyte sensor is configured to utilize the wireless data transmission apparatus to wirelessly transmit the at least one blood glucose level value to a data receiver device disposed internal to the body, the data receiver device being associated with a medicant delivery system.

27. The analyte sensor of claim 23, wherein the identification of the at least one of the plurality of glucose-modulated oxygen detectors which experiences unacceptable signal performance after the analyte sensor has been implanted in the tissue environment within the body comprises identification of at least one glucose-modulated detector whose performance degrades over a period of time, the period of time being within a time that the analyte sensor is implanted in the body.

28. An analyte sensor, comprising:
a biocompatible housing having a size and a shape suitable for implantation in a body;
a plurality of glucose-modulated oxygen detectors each comprising an enzymatic material, the enzymatic material enclosed in a membrane structure, the membrane structure configured to provide a barrier between biological tissues of the body and the enzymatic material at least when the analyte sensor is implanted in a tissue environment within the body;
circuitry operatively connected to the plurality of glucose-modulated oxygen detectors and configured to process signals generated by said plurality of glucose-modulated oxygen detectors to produce processed signals, the signals generated by each of the plurality of glucose-modulated oxygen detectors having a weight associated therewith;
wireless data transmission apparatus configured to transmit data relating to said processed signals; and
an electrical power source operatively coupled to at least the circuitry and the wireless data transmission apparatus and configured to provide electrical power thereto;
wherein said circuitry at least in part comprises processing logic which is configured to:
identify, after the analyte sensor has been implanted in the tissue environment within the body, at least one of the plurality of glucose-modulated oxygen detectors whose signal performance is experiencing progressive degradation;
based at least in part on the identification, progressively reduce over time a weight of signals generated by the identified at least one of the plurality of glucose-modulated oxygen detectors relative to weights of respective signals from others of the plurality of glucose-modulated oxygen detectors during generation of composite glucose-modulated signals such that the generated composite glucose-modulated signals are, over time, increasingly based on the others of the plurality of glucose-modulated oxygen detectors; and wherein the composite glucose-modulated signals are useful for calculation of a blood glucose level value.

29. The analyte sensor of claim 28, wherein the processing logic is further configured to:

utilize the composite glucose-modulated signals to calculate at least one blood glucose level value; and cause utilization of the wireless data transmission apparatus to wirelessly transmit the at least one blood glucose level value to a data receiver device disposed external to the body.

30. The analyte sensor of claim 28, wherein the analyte sensor is configured to utilize the wireless data transmission apparatus to wirelessly transmit at least one blood glucose level value to a data receiver device disposed internal to the body, the data receiver device being associated with a medicant delivery system, the at least one blood glucose level determined based at least on the composite glucose-modulated signals, the at least one blood glucose value useful in determining a medicant dose to be administered by the delivery system.

31. The analyte sensor of claim 28, wherein (i) the identification of the at least one of the plurality of glucose-modulated oxygen detectors whose signal performance is experiencing progressive degradation, and (ii) the progressive reduction over time of the weight of signals, cooperate to enable an increased accuracy of a blood glucose level determined based at least on the composite glucose-modulated signals.

32. A method of operating an implanted analyte sensor having a plurality of glucose-modulated analyte detectors comprising at least one enzymatic material enclosed in a membrane structure, the membrane structure configured to provide a barrier between biological tissues of a body within which the analyte sensor is implanted and the at least one enzymatic material, the method comprising:

identifying, during a period of implantation, one or more of the plurality of glucose-modulated analyte detectors which experience unacceptable signal variations;

based at least in part on the identification, selectively removing first signals generated by the identified one or more of the plurality of glucose-modulated analyte detectors from inclusion in a composite analyte detector signal; and generating the composite analyte detector signal from second signals generated by one or more remaining non-identified ones of the plurality of glucose-modulated analyte detectors which have not experienced the unacceptable signal variations.

33. The method of claim 32, further comprising using at least the generated composite analyte detector signal to calculate a blood glucose level value.

34. The method of claim 33, wherein the using the at least the generated composite analyte detector signal to calculate a blood glucose level value comprises using computerized logic of the implanted analyte sensor to calculate the blood glucose level.

35. The method of claim 34, wherein the analyte sensor is fully implanted within the body, and the method further comprises wirelessly transmitting the calculated blood glucose level from the fully implanted analyte sensor to a receiver apparatus disposed external to the body.

36. The method of claim 32, wherein the identifying the one or more of the plurality of glucose-modulated analyte detectors comprises determining that analyte migration into the one or more of the plurality of glucose-modulated analyte detectors is at least partially impeded.

37. The method of claim 32, wherein the identifying the one or more of the plurality of glucose-modulated analyte detectors comprises:

identifying an electrical failure of the one or more of the plurality of glucose-modulated analyte detectors; and deactivating the identified one or more of the plurality of glucose-modulated analyte detectors via circuitry of the implanted analyte sensor so as to at least mitigate stimulation of body response at an implantation site of the analyte sensor.

38. The method of claim 32, wherein:

each of the plurality of glucose-modulated analyte detectors comprises an active sensor and a reference sensor, and wherein the identifying the one or more of the plurality of analyte detectors comprises determining that at least one of the active sensor or the reference sensor of each of the one or more of the plurality of analyte detectors is inoperative; and the selectively removing comprises deactivating both the active sensor and the reference sensor of each of the one or more of the plurality of analyte detectors.

39. The method of claim 32, wherein:

the selectively removing comprises selectively decreasing a weight value associated with the first signals during the generation of the composite analyte detector signal; and the method further comprises selectively increasing a weight value associated with the second signals during the generation of the composite analyte detector signal.

40. The method of claim 39, wherein the selectively decreasing the weight value associated with the first signals comprises progressively decreasing the weight value associated with the first signals over a time of operation of the analyte sensor while implanted.

41. A method of operating a fully implanted analyte sensing device so as to extend a useful implanted operating lifetime of the analyte sensing device within a tissue environment of a body, the analyte sensing device comprising a plurality of glucose-modulated detectors, the method comprising:

identifying, when the analyte sensor is implanted in the tissue environment of the body, at least one of the plurality of glucose-modulated detectors which provide degraded glucose-modulated signals;

based at least in part on the identifying, selectively either (i) reducing a weighting associated with, or (ii) removing, glucose-modulated signals generated by the identified at least one of the plurality of glucose-modulated detectors from processing to generate a composite glucose-modulated signal, the reducing weighting or removing increasing an accuracy of the composite glucose-modulated signal relative to a composite glucose-modulated signal generated without the reducing weighting or removing, the increased accuracy enabling said extension of the useful implanted operating lifetime.

42. An implantable analyte sensor, comprising:

a biocompatible housing having a size and a shape each suitable for implantation in a body;

a sensing region comprising at least a plurality of enzymatic analyte detectors;

circuitry operatively connected to the plurality of enzymatic analyte detectors and configured to process at least a portion of signals generated by one or more of the plurality of enzymatic analyte detectors to produce processed signals;

wireless data transmission apparatus configured to transmit data to a receiver at least when the implanted analyte sensor is disposed in a tissue environment within said body;

an electrical power source operatively coupled to at least the circuitry and the wireless data transmission apparatus and configured to provide electrical power thereto; and at least one membrane apparatus associated with each of the plurality of enzymatic analyte detectors, the at least one membrane apparatus configured to, when the implantable analyte sensor is disposed in the tissue environment within the body, both (i) at least mitigate vascularization therein, and (ii) permit migration of blood analyte therethrough;

wherein the circuitry at least in part comprises processing logic configured to:

identify at least one of the plurality of enzymatic analyte detectors with degraded performance, the degraded performance caused by changing of an interface between the at least one enzymatic analyte detector and surrounding tissue of the body, the changing of the interface due to one or more biological processes within the body;

based at least in part on the identification, selectively either reduce a weighting of or remove signals generated by the identified at least one enzymatic analyte detector from processing of a composite signal; and generate the composite signal from other signals respectively produced by one or more remaining non-identified ones of the plurality of enzymatic analyte detectors.

43. The implantable analyte sensor of claim 42, wherein each of the enzymatic analyte detectors comprise a porous crosslinked protein-based material having a plurality of pores of a prescribed pore diameter at least on an outer surface of the at least one membrane apparatus, the plurality of pores of the prescribed pore diameter configured to enable said (i) mitigation of vascularization therein, and (ii) migration of blood analyte therethrough.

* * * * *